(12) United States Patent
Mody et al.

(10) Patent No.: US 7,112,671 B2
(45) Date of Patent: Sep. 26, 2006

(54) NON-SYMMETRIC TRIPYRRANES IN THE SYNTHESIS OF NOVEL MACROCYCLES

(75) Inventors: Tarak D. Mody, Sunnyvale, CA (US); Joshua Galanter, Brookline, MA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 441 days.

(21) Appl. No.: 10/363,401

(22) PCT Filed: Aug. 28, 2001

(86) PCT No.: PCT/US01/26755

§ 371 (c)(1),
(2), (4) Date: Feb. 26, 2003

(87) PCT Pub. No.: WO02/17925

PCT Pub. Date: Mar. 7, 2002

(65) Prior Publication Data
US 2003/0232800 A1    Dec. 18, 2003

Related U.S. Application Data

(60) Provisional application No. 60/229,247, filed on Aug. 30, 2000.

(51) Int. Cl.
C07D 487/22     (2006.01)
C07B 47/00      (2006.01)
C07F 5/10       (2006.01)

(52) U.S. Cl. .................. 540/145; 540/465; 540/472; 536/17.1; 536/17.3; 536/17.4; 534/15

(58) Field of Classification Search ............... 540/145, 540/465, 472; 536/17.1, 17.3, 17.4; 534/15
See application file for complete search history.

(56) References Cited

U.S. PATENT DOCUMENTS

| | | | |
|---|---|---|---|
| 4,935,498 A | 6/1990 | Sessler et al. ............... 534/15 |
| 5,041,078 A | 8/1991 | Matthews et al. | |
| 5,051,523 A | 9/1991 | Peter et al. ................. 556/147 |
| 5,120,411 A | 6/1992 | Sessler et al. ......... 204/157.15 |
| 5,159,065 A | 10/1992 | Sessler et al. ............... 534/15 |
| 5,162,509 A | 11/1992 | Sessler et al. ............... 534/15 |
| 5,252,720 A | 10/1993 | Sessler et al. ............... 534/11 |
| 5,256,399 A | 10/1993 | Sessler et al. ................. 424/9 |
| 5,272,142 A | 12/1993 | Sessler et al. ............... 514/185 |
| 5,292,414 A | 3/1994 | Sessler et al. ......... 204/157.5 |
| 5,302,714 A | 4/1994 | Sessler et al. ............... 540/472 |
| 5,369,101 A | 11/1994 | Sessler et al. ............... 534/13 |
| 5,373,093 A | 12/1994 | Vallarino et al. ............. 534/15 |
| 5,432,171 A | 7/1995 | Sessler et al. ............... 514/185 |
| 5,439,570 A | 8/1995 | Sessler et al. ......... 204/157.15 |
| 5,451,576 A | 9/1995 | Sessler et al. ............... 514/185 |
| 5,457,183 A | 10/1995 | Sessler et al. ............... 534/11 |
| 5,457,195 A | 10/1995 | Sessler et al. ............... 540/472 |
| 5,475,104 A | 12/1995 | Sessler et al. ............... 540/472 |
| 5,504,205 A | 4/1996 | Sessler et al. ............... 540/474 |
| 5,525,325 A | 6/1996 | Sessler et al. ............... 424/9.6 |
| 5,530,123 A | 6/1996 | Sessler et al. ............... 540/474 |
| 5,543,514 A | 8/1996 | Sessler et al. ............... 540/472 |
| 5,559,207 A | 9/1996 | Sessler et al. ............... 530/300 |
| 5,565,552 A | 10/1996 | Magda et al. ................. 534/11 |
| 5,567,687 A | 10/1996 | Magda et al. ................. 514/44 |
| 5,569,759 A | 10/1996 | Sessler et al. ............... 540/472 |
| 5,580,543 A | 12/1996 | Sessler et al. ............... 424/9.34 |
| 5,583,220 A | 12/1996 | Sessler et al. ............... 540/472 |
| 5,587,371 A | 12/1996 | Sessler et al. ............... 514/185 |
| 5,587,463 A | 12/1996 | Sessler et al. ............... 534/15 |
| 5,587,478 A | 12/1996 | Sessler et al. ............... 540/474 |
| 5,591,422 A | 1/1997 | Hemmi et al. ............. 424/9.362 |
| 5,594,136 A | 1/1997 | Sessler et al. ............... 540/472 |
| 5,595,726 A | 1/1997 | Magda et al. ............... 424/9.61 |
| 5,599,923 A | 2/1997 | Sessler et al. ................ 540/45 |
| 5,599,928 A | 2/1997 | Hemmi et al. ............... 540/474 |
| 5,601,802 A | 2/1997 | Hemmi et al. ............. 424/9.363 |
| 5,607,924 A | 3/1997 | Magda et al. ................. 514/44 |
| 5,622,946 A | 4/1997 | Sessler et al. ............... 514/185 |
| 5,672,490 A | 9/1997 | Sessler et al. ............... 435/91.1 |
| 5,696,240 A | 12/1997 | Vallarino et al. ............. 534/15 |
| 5,714,328 A | 2/1998 | Magda et al. ................. 435/6 |
| 5,775,339 A | 7/1998 | Woodburn et al. .......... 128/898 |
| 5,776,925 A | 7/1998 | Young et al. ................ 514/185 |

(Continued)

FOREIGN PATENT DOCUMENTS

WO    WO 90/10633    9/1990    .................. 487/22

(Continued)

OTHER PUBLICATIONS

Sessler et al., "Texaphyrins: Synthesis and Applications," Accounts of Chemical Research, vol. 27, No. 2, pp. 43-50 (1994).

(Continued)

Primary Examiner—James O. Wilson
Assistant Examiner—Paul V. Ward
(74) Attorney, Agent, or Firm—Wilson, Sonsini, Goodrich & Rosati

(57) ABSTRACT

The present invention provides certain non-symmetric tripyrranes; that is, tripyrranes that do not contain a mirror plane of symmetry perpendicular to the plane containing the tripyrrane. Further, the invention includes texaphyrin compounds and sapphyrin compounds, as well as other polypyrrolic macrocycles, prepared using tripyrranes of Formula I as a precursor. These macrocycles are characterized by a tripyrrolic portion of the macrocyclic ring having substituents that cause the heterocycle to lack a plane of symmetry perpendicular to the plane of the macrocycle.

5 Claims, No Drawings

U.S. PATENT DOCUMENTS

| | | | |
|---|---|---|---|
| 5,798,491 A | 8/1998 | Magda et al. | 204/157.15 |
| 5,886,173 A | 3/1999 | Hemmi et al. | 540/472 |
| 6,072,038 A * | 6/2000 | Sessler et al. | 530/391.7 |

FOREIGN PATENT DOCUMENTS

| | | | |
|---|---|---|---|
| WO | WO 94/09003 | 4/1994 | 487/22 |
| WO | WO 94/29316 | 12/1994 | 487/22 |
| WO | WO 95/10307 | 4/1995 | 51/4 |
| WO | WO 95/21845 | 8/1995 | 487/22 |
| WO | WO 96/09315 | 3/1996 | |
| WO | WO 96/38461 | 12/1996 | |
| WO | WO 96/40253 | 12/1996 | |
| WO | WO 97/26915 | 7/1997 | |
| WO | WO 97/35617 | 10/1997 | |
| WO | WO 97/46262 | 12/1997 | 47/48 |
| WO | WO 98/07733 | 2/1998 | |

OTHER PUBLICATIONS

Yougn et al., "Experimental Acute Cerebral Ischemia with Reperfusion: Evaluation with Gadolinium-Texaphyrin," Investigative Radiology, vol. 31, No. 6, pp. 353-358 (1996).

Young et al., "Gadolinium(III) texaphyrin: A Tumor Selective Radiation Sensitizer that is Detectable by MRI," Proc. Natl. Acad., vol. 93, pp. 6610-6615 (1996).

Young et al., "Imaging of Human Colon Cancer Xenograft with Gadolinium-Texaphyrin," Investigative Radiology, vol. 31, No. 5, pp. 280-283 (1996).

PCT Notification of Transmittal of International Search Report, dated Dec. 13, 2001.

* cited by examiner

NON-SYMMETRIC TRIPYRRANES IN THE SYNTHESIS OF NOVEL MACROCYCLES

CLAIM OF PRIORITY

This application claims the benefit of priority from International Patent Application PCT/US01/26755, filed Aug. 28, 2001, which claims the benefit of priority from U.S. Provisional Application No. 60/229,247, filed Aug. 30, 2000, both of which are incorporated herein, by reference, in their entirety.

FIELD OF THE INVENTION

The present invention relates to certain non-symmetric tripyrranes, their preparation, their use as intermediates in synthesizing polypyrrole macrocycles, and the novel polypyrrole macrocycles derived from such intermediates.

BACKGROUND INFORMATION

Substituted tripyrranes have been recognized as important building blocks for synthesizing a wide variety of polypyrrolic macrocycles. See, for example, PCT Publication WO 97/32884 for a description of previously known tripyrranes, their methods of synthesis and use in preparing macrocyclic compounds. Previously known tripyrranes have in general been symmetrical. Symmetrical in this context means, for example, that in the tripyrrane compound represented by Formula A below:

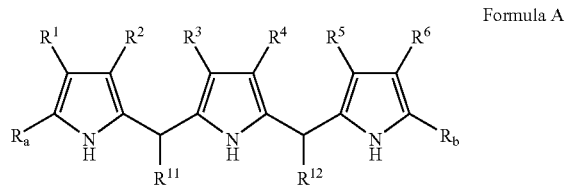

Formula A $R^1$ is the same as $R^6$, $R^2$ is the same as $R^5$, and $R^3$ is the same as $R^4$, and accordingly there is a plane of symmetry between $R^3$ and $R^4$.

In those cases known in the art where the tripyrranes have been partially symmetric, the requirements of the prior art syntheses dictate that the dissymmetry arises solely at the center pyrrole, and not from the two outer pyrroles, which are the same as above. That is, $R^1$ is the same as $R^6$, and $R^2$ is the same as $R^5$, but $R^3$ is no longer the same as $R^4$. For partially symmetric tripyrranes of this nature, see Cavaleiro, J. A. C. S., et al., J.Chem.Soc., Perkin Trans 1, 21:2471–2478, 1973; Sessler, J. L., et al., Synlett, 2:187–188, 1996; Rocha Gonsalves, A. M. D'A., et al., Tetrahedron Lett., 22:2203–2206, 1972.

Non-symmetric tripyrranes—that is, those tripyrranes of Formula A in which $R^1$ is not the same as $R^6$ and/or $R^2$ is not the same as $R^5$, and $R^3$ and $R^4$ are the same or different— have not been previously disclosed, nor has a process for their synthesis. The ability to synthesize non-symmetric tripyrranes would provide a route for the preparation of novel polypyrrole macrocycles having desirable biodistribution or pharmacokinetic properties. A process for the synthesis of non-symmetric tripyrranes has now been discovered.

SUMMARY OF THE INVENTION

The present invention provides certain non-symmetric tripyrranes having the following Formula I:

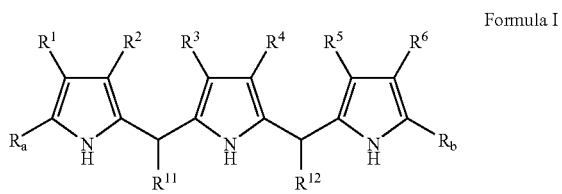

Formula I wherein:
$R^1$, $R^2$, $R^3$, $R^4$, $R^5$ and $R^6$ are independently chosen from hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, saccharide, optionally substituted amino, optionally substituted carboxyalkyl, optionally substituted carboxyamide, optionally substituted carboxyamidoalkyl, optionally substituted heterocycle, optionally substituted cycloalkyl, optionally substituted arylalkyl, optionally substituted heteroarylalkyl, optionally substituted heterocycloalkylalkyl; or a group —X—Y, in which X is a covalent bond or a linker and Y is a catalytic group, a chemotherapeutic agent, or a site-directing molecule;
$R^{11}$ and $R^{12}$ are independently hydrogen, optionally substituted alkyl, optionally substituted aryl, optionally substituted alkoxy, optionally substituted carboxyalkyl, or optionally substituted carboxyamidealkyl; and
$R_a$ and $R_b$ are both hydrogen, —C(O)R', —CO$_2$R', or —CHR'-L where R' is hydrogen, optionally substituted alkyl, or optionally substituted aryl; and L is a leaving group; with the proviso that $R^1$ is different from $R^6$, and/or $R^2$ is different from $R^5$.

Further included in the invention are methods for synthesizing the compounds of Formula I. Specifically, a preferred method for making a compound of Formula I comprises reacting a symmetric or non-symmetric tripyrrane dicarboxylic acid or diester, synthesized by methods known in the art, with a strong acid to effect decarboxylation, resulting in an acid-catalyzed pyrrole rearrangement to a mixture of tripyrranes, which are reacted in-situ with a formylating agent, for example triethylorthoformate, and the products separated and purified to give the desired compound of Formula I. A second method for making a compound of Formula I comprises the steps of condensing a first pyrrole with a second pyrrole to give a dipyrromethane, which is then condensed with a third pyrrole to give the non-symmetric tripyrrane of Formula I. This second method is sometimes referred to herein as the "1+1+1" addition or synthesis or synthetic route.

The non-symmetric tripyrranes of Formula I can be used to synthesize a wide variety of different polypyrrole macrocycles, including for example synthetic porphyrins, porphyrins analogues, expanded porphyrins (such as, for example, pentaphyrins, texaphyrins, sapphyrins, and hexaphyrins), as well as other related polypyrrole macrocycles, and polyazamacrocycles. Preferred are texaphyrins and sapphyrins Most preferred are the metallotexaphyrins shown below as Formula II, where $R^1$ is different from $R^6$, and/or $R^2$ is different from $R^5$.

Formula II

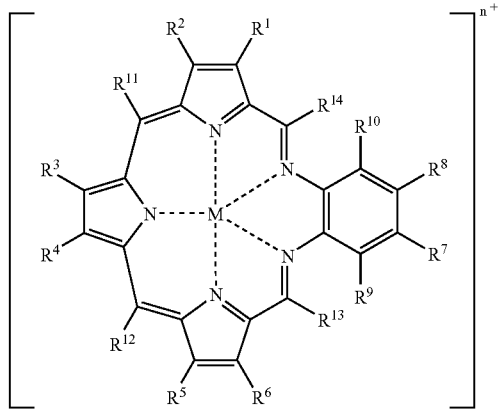

wherein

M is a monovalent, divalent, trivalent, or tetravalent metal cation;

$R^1$, $R^2$, $R^3$, $R^4$, $R^5$, $R^6$, $R^7$, and $R^8$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, optionally substituted haloalkyl; nitro, acyl, optionally substituted alkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl, and the group —X—Y, in which X is a covalent bond or a linker and Y is a catalytic group, a chemotherapeutic agent, or a site-directing molecule; and $R^9$, $R^{10}$, $R^{11}$, $R^{12}$, $R^{13}$ and $R^{14}$ are independently hydrogen, optionally substituted alkyl, optionally substituted aryl, optionally substituted alkoxy, optionally substituted carboxyalkyl, or optionally substituted carboxyamidealkyl;

with the proviso that the halogen is other than iodide and the haloalkyl is other than iodoalkyl; with the further proviso that $R^1$ is different from $R^6$, and/or $R^2$ is different from $R^5$; and AL is an apical ligand; and n is an integer of 1–5.

Generally speaking, the preparation of substituted polypyrrolic macrocycles includes two principal steps: (a) an acid-catalyzed cyclization step of a compound of Formula I, which can include the use of a cyclization agent, and (b) an oxidation step, which is optionally carried out concurrently with a metallation step, to form a fully conjugated macrocycle or metallmacrocycle. Such synthetic methods are known in the art. For example, a texaphyrin may be prepared by condensation of o-phenylenediamine with a non-symmetric tripyrrane of Formula I, and a sapphyrin may be prepared by condensation of a bipyrrole with a non-symmetric tripyrrane of Formula I.

DETAILED DESCRIPTION OF THE INVENTION

The non-symmetric tripyrranes of the invention, the compounds of Formula I, are as shown above. The substituents $R^1$ through $R^6$ are chosen independently, and may be the same or different, with the proviso that $R^1$ is different from $R^6$ and/or $R^2$ is different from $R^5$.

The preferred process for their preparation involves an initial decarboxylation of a tripyrrane-α,α'-dicarboxylate in the presence of a strong acid. Without wishing to be bound by theory, it is believed that the compound formed by decarboxylation (the α,α'-dihydro equivalent) is labile, and, under acid catalysis, one terminal pyrrole decouples from the tripyrrane to give a dipyrromethane and a pyrromethyl cation. This cation is able to recouple to either α-position of the dipyrromethane, and consequently re-addition of the pyrromethyl cation leads to a mixture of tripyrranes, one of which is the desired non-symmetric tripyrrane of the invention.

Alternatively, the non-symmetric tripyrranes of Formula I can be prepared by the "1+1+1" synthetic methods shown below as Reaction Schemes 2 and 3, in which an appropriately substituted pyrrole is reacted with a second pyrrole to give a dipyrrane product, which is reacted with a third pyrrole to give a compound of Formula I.

Definitions

As used in the present specification and the appended claims, the following words and phrases are generally intended to have the meanings as set forth below, except to the extent that the context in which they are used indicates otherwise.

The terms "a" and "an" mean "one or more" when used herein.

The term "compound of Formula II" and "compound of Formula III" is intended to encompass the metallotexaphyrins and sapphyrins of the invention as disclosed, coordination complexes of the compounds of Formula II and III, and/or the pharmaceutically acceptable salts of such compounds.

The term "effective amount" or "therapeutically effective amount" refers to that amount of a compound of Formula II or III that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose will vary depending on the particular compound of Formula II or III chosen, the dosing regimen to be followed, timing of administration, the tissue to be imaged, and the physical delivery system in which it is carried.

For purposes of this invention, "non-symmetric" as used in connection with the compounds of Formula I:

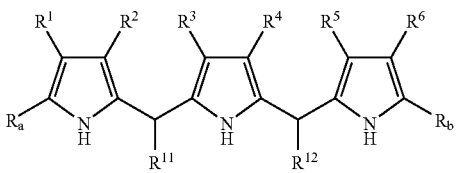

describes those compounds of Formula I in which $R^1$ is not the same as $R^6$ and/or $R^2$ is not the same as $R^5$, and $R^3$ and $R^4$ are the same or different.

"Polypyrrole macrocycles" refers to compounds that are cyclic in structure and include within their ring structure at least three pyrroles. Such compounds include, for example, porphyrins, substituted porphyrins, synthetic porphyrins, and porphyrin derivatives (such as chlorins, e.g.). Also included are "expanded porphyrins" such as texaphyrins, sapphyrins, smagdyrins, pentaphyrins, hexaphyrins, and anthraphyrins, among others.

"Texaphyrin" means an aromatic pentadentate macrocyclic expanded porphyrin, also described as an aromatic benzannulene containing both 18π- and 22π-electron delocalization pathways. Texaphyrins and water-soluble texaphyrins, methods of preparation, and various uses have been described in, for example, U.S. Pat. Nos. 4,935,498; 5,162,509; 5,252,720; 5,256,399; 5,272,142; 5,292,414; 5,369,101; 5,432,171; 5,439,570; 5,451,576; 5,457,183; 5,475,104; 5,504,205; 5,525,325; 5,559,207; 5,565,552; 5,567,687; 5,569,759; 5,580,543; 5,583,220; 5,587,371; 5,587,463; 5,591,422; 5,594,136; 5,595,726; 5,599,923; 5,599,928; 5,601,802; 5,607,924; 5,622,946; and 5,714,328; International (PCT) Publications WO 90/10633, 94/29316, 95/10307, 95/21845, 96/09315, 96/40253, 96/38461, 97/26915, 9735617, 97/46262, and 98/07733; and allowed U.S. patent application Ser. Nos. 08/458,347, 08/591,318, 08/903,121, and 08/914,272; each patent, publication, and application is incorporated herein by reference.

The texaphyrins or metallotexaphyrins according to the present invention are shown below as Formula II, where $R^1$ is different from $R^6$, and/or $R^2$ is different from $R^5$.

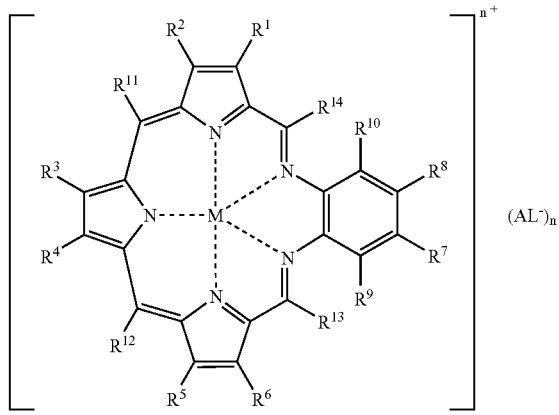

Formula II wherein
M is a monovalent, divalent, trivalent, or tetravalent metal cation;

$R^1$, $R^2$, $R^3$ $R^4$, $R^5$, $R^6$, $R^7$, and $R^8$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, optionally substituted haloalkyl; nitro, acyl, optionally substituted alkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl, and the group —X—Y, in which X is a covalent bond or a linker and Y is a catalytic group, a chemotherapeutic agent, or a site-directing molecule; and $R^9$, $R^{10}$, $R^{11}$, $R^{12}$, $R^{13}$ and $R^{14}$ are independently hydrogen, optionally substituted alkyl, optionally substituted aryl, optionally substituted alkoxy, optionally substituted carboxyalkyl, or optionally substituted carboxyamidealkyl; with the proviso that the halogen is other than iodide and the haloalkyl is other than iodoalkyl; with the further proviso that $R^1$ is different from $R^6$, and/or $R^2$ is different from $R^5$; and AL is an apical ligand; and
n is an integer of 1–5.

M may be monovalent, divalent, trivalent, or tetravalent. Examples of monovalent metal cations are tellurium and technetium; an example of an appropriate tetravalent metal is thorium. Preferred are divalent and trivalent metals. Preferred divalent metal cations are Ca(II), Mn(II), Co(II), Ni(II), Zn(II), Cd(II), Hg(II), Fe(II), Sm(II), or U(II). Preferred trivalent metal cations are Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), or U(III). More preferred trivalent metal cations are Lu(III) or Gd(III). In some embodiments, in particular for use in neutron capture therapy, the metal can be present as a pure isotope of the metal, or be enriched in one or more of its isotopes. For example, gadolinium may be present as its $^{155}$Gd or $^{157}$Gd isotope, or "natural" gadolinium may be optionally enriched in the isotopes $^{155}$Gd and/or $^{157}$Gd. Similarly, cadmium may be present as the cadmium isotope $^{113}$Cd, or "natural" cadmium enriched in $^{113}$Cd; europium may be present as the europium isotope $^{151}$Eu, or "natural" europium enriched in $^{151}$Eu; mercury may be present as the mercury isotope $^{199}$Hg, or "natural" mercury enriched in $^{199}$Hg; and samarium may be present as the samarium isotope $^{149}$Sm. or "natural" samarium enriched in $^{149}$Sm. Particularly preferred for neutron capture therapy is the $^{157}$Gd isotope of gadolinium, or "natural" gadolinium enriched in the isotope $^{157}$Gd.

M or one of groups $R^1$ to $R^{12}$ can optionally be radioactive, and are as described in the U.S. Patents, PCT publications, and allowed and pending patent applications disclosed and incorporated by reference below.

In the texaphyrins of the present invention, when M is a divalent cation it is preferably selected from the group consisting of Ca(II), Mn(II), Co(II), Ni(II), Zn(II), Cd(II), Hg(II), Fe(II), Sm(II) and UO$_2$ (II), or when M is a trivalent metal cation it is preferably selected from the group consisting of Mn(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III).

When M is a divalent metal cation, typically n is 1, and when M is a trivalent metal cation, typically n is 2. AL may be, for example, chloride, nitrate, acetate, and hydroxide, carboxylates of sugar derivatives, such as gluconic acid or glucoronic acid, cholesterol derivatives such as cholate and deoxycholate, PEG acids, organic acids such as formic acid, acetic acid, propionic acid, benzoic acid, 3,6,9-trioxodecanoic acid, 3,6-dioxoheptanoic acid, methylvaleric acid, organophosphates, or inorganic acids, and the like.

It should be understood that the complexes described in the present invention may have one or more additional ligands providing coordinative saturation to the metal ion. Such ligands include pyridine, benzimidazole, methanol, water, and the like.

"Sapphyrins" and water-soluble sapphyrins and methods of preparation have been described in U.S. Pat. Nos. 5,041,078; 5,120,411; 5,159,065; 5,302,714; 5,457,195; 5,530,123; 5,543,514; and 5,672,490; and in International Publn. WO 94/09003; all of which are incorporated herein by reference.

Representative sapphyrins according to the present invention are shown below as Formula III, where $R^1$ is different from $R^6$, and/or $R^2$ is different from $R^5$:

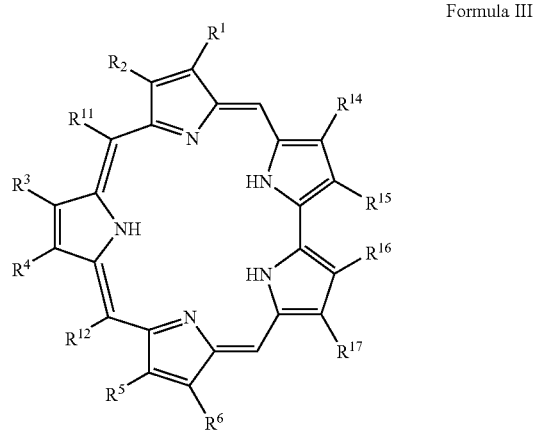

Formula III

In the sapphyrins of the present invention, each of $R^1$ through $R^6$, $R^{11}$ and $R^{12}$ are as defined above. $R^{14}$ through $R^{17}$ are defined in the same manner as $R^7$ through $R^{10}$ above. They may exist as a metal complex as shown above for texaphyrins.

"Synthetic porphyrins" are tetrapyrrolic macrocycles structurally similar to a porphyrin. Synthetic porphyrins may be substituted or unsubstituted; representative synthetic porphyrins are known in the art.

"Expanded porphyrins" are synthetic molecules having a ring structure composed at least in part of pyrroles. Examples of expanded porphyrins are known in the art and include, in addition to texaphyrins and sapphyrins, pentaphyrins, hexaphyrins, and anthraphyrins, for example. For the purposes of this invention, an expanded porphyrin will have a tripyrrolic fragment.

The term "alkyl" refers to a monoradical branched or unbranched saturated hydrocarbon chain preferably having from 1 to 20 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to (1) an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or (2) an alkyl group as defined above that is interrupted by 1–20 atoms independently chosen from oxygen, sulfur and NR$^a$—, where R$^a$ is chosen from hydrogen, or optionally substituted alkyl, cycloalkyl, alkenyl, cycloalkenyl, alkenyl, cycloalkenyl, alkynyl, aryl, heteroaryl and heterocyclic; or (3) an alkyl group as defined above that has both from 1 to 5 substituents as defined above and is also interrupted by 1–20 atoms as defined above.

One preferred alkyl substituent is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; and those compounds known as polyethylene glycols, polypropylene glycols and polybutylene glycols, and the like.

Another preferred alkyl substituent is halogen, exemplified by groups, such as 2-chloroethyl, 3-fluoropropyl, 3-bromobutyl, 4-fluorobutyl, and the like; dihaloalkyl groups such as 2,3-dichloropropyl, 3,4-difluorobutyl, 2-fluoro-4-bromobutyl, and the like.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to:

(1) an alkylene group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include those where two substituents on the alkylene group are fused to form one or more cycloalkyl, substituted cycloalkyl, cycloalkenyl, substituted cycloalkenyl, aryl, heterocyclic or heteroaryl groups fused to the alkylene group; or (2) an alkylene group as defined above that is interrupted by 1–20 atoms independently chosen from oxygen, sulfur and NR$^a$—, where R$^a$ is chosen from hydrogen, optionally substituted alkyl, cycloalkyl, alkenyl, cycloalkenyl, alkenyl, cycloalkenyl, alkynyl, aryl, heteroaryl and heterocyclic, or groups selected from carbonyl, carboxyester, carboxyamide and sulfonyl; or (3) an alkylene group as defined above that has both from 1 to 5 substituents as defined above and is also interrupted by 1–20 atoms as defined above.

Examples of substituted alkylenes are chloromethylene (—CH(Cl)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxyethoxy)ethane (—CH$_2$CH$_2$O—CH$_2$CH$_2$—OCH$_2$CH$_2$—OCH$_2$CH$_2$—), and the like.

The term "alkaryl" refers to the groups -optionally substituted alkylene-optionally substituted aryl, where alkylene, substituted alkylene, aryl and substituted aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein. One preferred substituted alkoxy group is substituted alkyl-O, and includes groups such as —OCH$_2$CH$_2$OCH$_3$, PEG groups such as —O(CH$_2$CH$_2$O)$_x$CH$_3$, where x is an integer of 2–20, preferably 2–10, and more preferably 2–5. Another preferred substituted alkoxy group is —O—CH$_2$—(CH$_2$)$_y$—OH, where y is an integer of 1–10, preferably 1–4.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 20 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (—C≡CCH$_3$), and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—CH$_2$—C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "cycloalkylene" refers to the diradical derived from cycloalkyl as defined above and is exemplified by 1,1-cyclopropylene, 1,2-cyclobutylene, 1,4-cyclohexylene and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "substituted cycloalkylene" refers to the diradical derived from substituted cycloalkyl as defined above.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "cycloalkenylene" refers to the diradical derived from cycloalkenyl as defined above and is exemplified by 1,2-cyclobut-1-enylene, 1,4-cyclohex-2-enylene and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "substituted cycloalkenylene" refers to the diradical derived from substituted cycloalkenyl as defined above.

The term "halo" or "halogen" refers to fluoro, chloro, bromo and iodo.

The term "heteroaryl" refers to an aromatic group comprising 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated or unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "heterocyclene" refers to the diradical group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups that contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "carboxyamides" include primary carboxyamides (CONH$_2$), secondary carboxyamides (CONHR') and tertiary carboxyamides (CONR'R"), where R' and R" are the same or different substituent groups chosen from alkyl, alkenyl, alkynyl, alkoxy, aryl, a heterocyclic group, a functional group as defined herein, and the like, which themselves may be substituted or unsubstituted.

"Carboxyamidoalkyl" means a carboxyamide as defined above attached to an optionally substituted alkylene group as defined above.

The term "saccharide" includes oxidized, reduced or substituted saccharides, including hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides; as well as open chain forms of sugars, and the like. Examples of amine-derivatized sugars are galactosamine, glucosamine, and sialic acid.

The term "site-directing molecule" refers to a molecule having an affinity for a biological receptor or for a nucleic acid sequence. Exemplary site-directing molecules useful herein include, but are not limited to, polydeoxyribonucleotides, oligodeoxyribonucleotides, polyribonucleotide analogs, oligoribonucleotide analogs, polyamides including peptides having affinity for a biological receptor and proteins such as antibodies, steroids and steroid derivatives, hormones such as estradiol or histamine, hormone mimics such as morphine, and further macrocycles such as sapphyrins and rubyrins. The oligonucleotides may be derivatized at the bases, the sugars, the ends of the chains, or at the phosphate groups of the backbone to promote in vivo stability. Modifications of the phosphate groups are preferred in one embodiment since phosphate linkages are sensitive to nuclease activity. Presently preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy or propoxy. The alkenyl group is preferably allyl. The alkyl group is preferably a methyl group and the methyl group is attached to the 2' oxygen of the ribose. Other alkyl groups may be ethyl or propyl. It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates, phosphoramidates and the like. Deoxyribonucleotides, deoxyribonucleotide analogs and ribonucleotide analogs are contemplated as site-directing molecules in the present invention. The term "texaphyrin-oligonucleotide conjugate" means that an oligonucleotide is attached to the texaphyrin in a 5' or a 3' linkage, or in both types of linkages to allow the texaphyrin to be an internal residue in the conjugate. It can also refer to a texaphyrin that is linked to an internal base of the oligonucleotide. The oligonucleotide or other site-directing molecule may be attached either directly to the texaphyrin or to the texaphyrin via a linker or a couple of variable length.

The term "catalytic group" means a chemical functional group that assists catalysis by acting as a general acid, Brønsted acid, general base, Brønsted base, nucleophile, or any other means by which the activation barrier to reaction is lowered or the ground state energy of the substrate is increased. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, $(LysAla)_n$, $(LysLeuAla)_n$ where n is from 1–30 or preferably 1–10 or more preferably 2–7 and the like; derivatives thereof; and metallotexaphyrin complexes.

A "chemotherapeutic agent" may be, but is not limited to, one of the following: an alkylating agent such as a nitrogen mustard, an ethyleneimine or a methylmelamine, an alkyl sulfonate, a nitrosourea, or a triazene; an antimetabolite such as a folic acid analog, a pyrimidine analog, or a purine analog; a natural product such as a vinca alkaloid, an epipodophyllotoxin, an antibiotic, an enzyme, taxane, or a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Chemotherapeutic agents are used in the treatment of cancer and other neoplastic tissue, and may also be antibacterials, antivirals, antifungals, and antiparasitic agents. Preferably, the chemotherapeutic agent is a nitrogen mustard, an epipodophyllotoxin, an antibiotic, or a platinum coordination complex. A more preferred chemotherapeutic agent is bleomycin, doxorubicin, taxol, taxotere, etoposide, 4-OH cyclophosphamide, cisplatin, or platinum coordination complexes analogous to cisplatin. A presently preferred chemotherapeutic agent is doxorubicin, taxol, taxotere, cisplatin, or Pt complexes analogous to cisplatin. Various chemotherapeutic agents, their target diseases, and treatment protocols are presented in, for example, Goodman and Gilman's The Pharmacological Basis of Therapeutics, Eighth Ed., Pergamon Press, Inc., 1990; and Remington: The Science and Practice of Pharmacy, Mack Publishing Co., Easton, Pa., 1995; both of which are incorporated by reference herein.

A site directing molecule, or a group having or catalytic or chemotherapeutic activity, identified above by the symbol Y, may be covalently coupled to any position on a macrocycle (for example a texaphyrin or a sapphyrin) by a covalent bond or by a linker (identified above by the symbol X). The term "linker" as used herein means a group that covalently connects Y to a macrocycle, and may be, for example, alkylene, alkenylene, alkynylene, arylene, ethers, PEG moieties, and the like, all of which may be optionally substituted. Examples of reactions to form a covalent link include reaction between an amine (on either the molecule Y or X) with a carboxylic acid (on the corresponding X or Y) to form an amide link. Similar reactions well known in the art are described in standard organic chemistry texts such as J. March, "Advanced Organic Chemistry", $4^{th}$ Edition, Wiley-Interscience, New York, 1992.

The term "apical ligand" means an anion that binds to the core metal with delocalized electrostatic bonds. The number of apical ligands (n) is defined as an integer of 1–5. It should be noted that the apical ligands act to neutralize the charge on the metallomacrocycle. For example, when the macrocycle is a texaphyrin, typically n is 1 when M is a divalent cation, and n is 2 when M is a trivalent cation (because the core itself neutralizes one unit charge). However, if any of $R^1$, $R^2$, $R^3$, $R^4$, $R^6$, $R^7$, $R^8$, $R^9$, $R^{10}$, $R^{11}$, and $R^{12}$ is capable of forming an anion, for example a carboxylic acid or a phosphate, then n will decrease appropriately. It is also possible that the apical ligands could have two functionalities capable of forming an anion, for example a dicarboxylic acid, and such ligands are intended to be within the scope of the invention. Apical ligands of texaphyrins are disclosed in more detail in U.S. patent application Ser. No. 09/941,924, Attorney Docket No. 4200.01 US, which is filed on an even date herewith, incorporated by reference herein.

It should be noted that in addition to the apical ligand substituents described above, it is also possible for the metal core to form coordination complexes with molecules such as pyridine, benzimidazole, water, and methanol.

The term "leaving group" means a group that is displaced under acid or nucleophilic attack. Examples are iodo, bromo, chloro, tosylate, mesylate, OAc, —NH$_2$, quarternary amines, for example a trimethylammonium iodide moiety, or hydroxy The term "optional" or "optionally" means that the subsequently described event or circumstance may or may not occur, and that the description includes instances in which said event or circumstance occurs and instances in which it does not. For example, "optionally substituted aryl" means that the aryl group may or may not be substituted and that the description includes both unsubstituted aryl and substituted aryl. As another example, "optionally converting the free base to the acid addition salt" means that such conversion may or may not be carried out in order for the process described to fall within the invention, and the invention includes those processes wherein the free base is converted to the acid addition salt and those processes in which it is not.

Nomenclature

The compounds of Formula I are named using the numbering system illustrated below.

5. 1,14-formyl-12-propyl-2,3,7 triethyl-8,13-dimethyltripyrrane

Similarly, compounds of the formula:

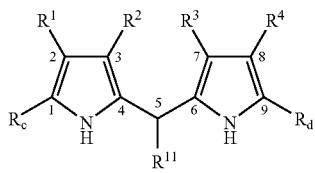

are named as dipyrranes using the numbering system as shown above.

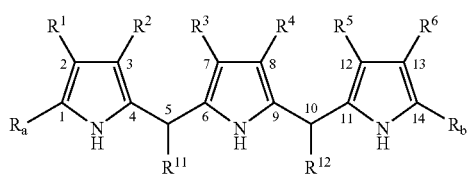

I

Following are examples of some representative compounds of Formula I where R$^{11}$ and R$^{12}$ are both hydrogen:

| No. | R$_a$ & R$_b$ R$^6$ | R$^1$ | R$^2$ | R$^3$ | R$^4$ | R$^5$ |
|---|---|---|---|---|---|---|
| 1. | CHO CH$_3$ | CH$_2$CH$_3$ | CH$_2$CH$_3$ | CH$_2$CH$_2$CH$_2$OH | CH$_3$ | CH$_2$CH$_2$CH$_2$OH |
| 2. | COOH CH$_3$ | CH$_2$CH$_3$ | CH$_2$CH$_3$ | CH$_2$CH$_2$CH$_2$OH | CH$_3$ | CH$_2$CH$_2$CH$_2$OH |
| 3. | H CH$_3$ | CH$_2$CH$_3$ | CH$_2$CH$_3$ | CH$_2$CH$_2$CH$_2$OH | CH$_3$ | CH$_2$CH$_2$CH$_2$OH |
| 4. | CHO CH$_2$COOH | Et$_2$NCH$_2$ | (CH$_2$)$_3$OH | (CH$_2$)$_2$NHC(O)CH$_2$NH$_2$ | CH$_3$ | C(O)CH$_3$ |
| 5. | CHO CH$_3$ | CH$_2$CH$_3$ | CH$_2$CH$_3$ | CH$_2$CH$_3$ | CH$_3$ | (CH$_2$)$_2$CH$_3$ | and they are named:

1. 2,3-diethyl-1,14-diformyl-7,12-bis(3-hydroxypropyl)-8,13-dimethyltripyrane [alternatively named 2,3-diethyl-7,12-bis(3-hydroxypropyl)-8,13-dimethyltripyrrane 1,14-dialdehyde; or 2,3-diethyl-7,12-di(3-hydroxypropyl)-8,13-dimethyltripyrrane α,α'-dialdehyde];

2. 1,14-dicarboxyl-2,3-diethyl-7,12-bis(3-hydroxypropyl)-8,13-dimethyltripyrrane 3. 2,3-diethyl-7,12-bis(3-hydroxypropyl)-8,13-dimethyltripyrrane 4. 12-acetyl-1,14-diformyl-2-diethylamino-7-(2-glycinylaminoethyl)-3-(3-hydroxypropyl)-8-methyltripyrrane-13-acetic acid;

For example, a compound of the formula:

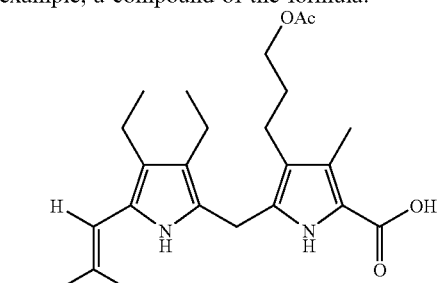

is named as:

7-(3-acetoxypropyl)-1-(2-cyanoacrylic acid ethyl ester)-2,3-diethyl-8-methyldipyrrane-9-carboxylic acid.

The naming and numbering of the compounds of Formula II is illustrated with a representative compound texaphyrin in which AL is acetate, and the metal M is lutetium (Lu):

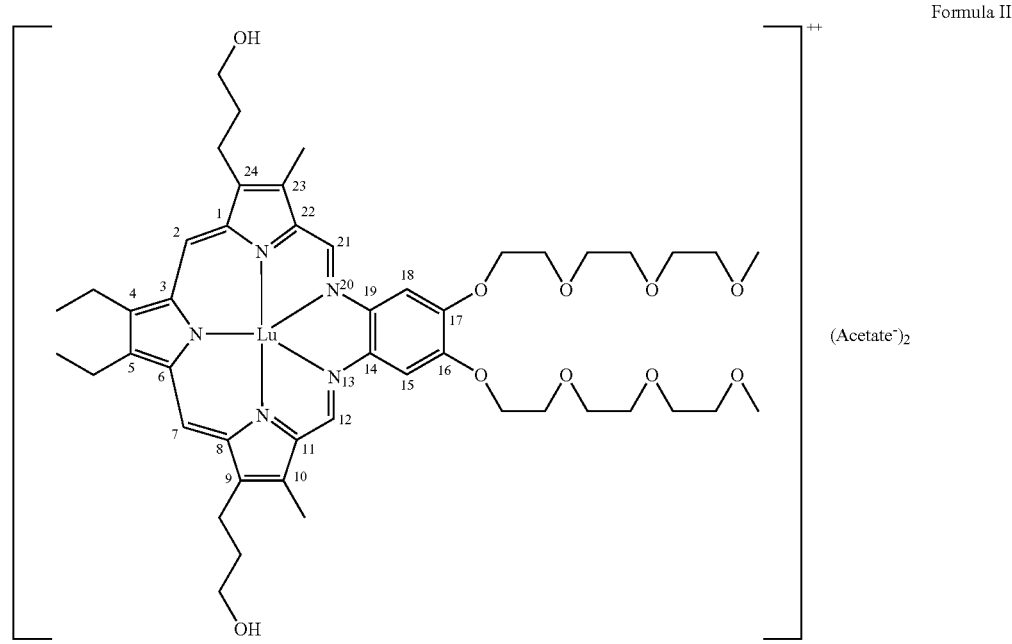

Formula II (Acetate⁻)₂

This compound can be named in a variety of ways (e.g. depending on the origination of the numbering). A preferred name is:

The lutetium (III) complex of: 4,5-diethyl-10,23-dimethyl-9,24-bis(3-hydroxy propyl)-16,17-bis[2-[2-(2 methoxyethoxy)ethoxy]ethoxy]pentaazapentacyclo[20.2.1.1$^{3,6}$.1$^{8,11}$.0$^{14,19}$]heptacos a-1,3,5,7,9,11(27),12,14,16,18,20,22(25),23-tridecaene bis acetate; or Synthetic Reaction Parameters The terms "solvent", "inert organic solvent" and "inert solvent" mean a solvent inert under the conditions of the reaction being describe d in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine, and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

The reaction temperature can vary widely depending on the reactivity of the reactants. However, the temperature should not be so high as to decompose the reactants or so low as to cause inhibition of the reaction or otherwise interfere with the reaction. Unless specified to the contrary, the reactions described herein take place at atmospheric pressure over a temperature range from about −70°–100° C., more preferably from about 10° C. to about 50° C. (or the reflux temperature of the solvent employed), and most preferably at "room" or "ambient" temperature ("RT"), e.g. about 20° C.

Unless otherwise specified, the reaction times and conditions are intended to be approximate.

The time required for the reactions herein will depend to a large extent on the temperature being used and the relative reactivities of the starting materials. Therefore, the reaction time can vary greatly, for example from about five minutes to about two days. Various known techniques such as different types of chromatography, especially thin layer chromatography ("TLC"), gas chromatography ("GC"), HPLC, or optical spectroscopy can be used to follow the progress of the reaction by the disappearance of the starting compound(s).

Isolation and purification of the compounds and intermediates described herein can be effected, if desired, by any suitable separation or purification procedure such as, for example, filtration, extraction, crystallization, distillation, normal or reverse-phase column chromatography, thin-layer chromatography, thick-layer chromatography, centrifugal chromatography, or preparatory or semi-preparatory HPLC, or a combination of these procedures. Specific illustrations of suitable separation and isolation procedures can be found by reference to the examples hereinbelow. However, other equivalent separation or isolation procedures can, of course, also be used.

Synthesis of Compounds of Formula I

The compounds of Formula I can be prepared by different synthetic routes. In a first preferred method, the non-symmetric tripyrranes are synthesized by an acid-catalyzed rearrangement of symmetric tripyrranes. In a second preferred method, non-symmetric tripyrranes are synthesized by "1+1+1" addition of pyrroles, or an addition of a pyrrole to a dipyrromethane. The alternative syntheses are described below with reference to Reaction Schemes 1 through 3.

Brief Description of Reaction Schemes

Reaction Scheme 1 illustrates the synthesis of the compounds of Formula I. The synthesis starts from a symmetric tripyrrane-1,14-dicarboxylic acid of formula 101, in which $R^3$ is the same as $R^5$, $R^4$ is the same as $R^6$, and $R^1$ and $R^2$ are either the same or different.

Reaction Scheme 2 illustrates the synthesis of the compounds of Formula I (a 1,14-dialdehyde) via a "1+1+1" addition of individual pyrroles. Each of $R^1$ through $R^6$ is independent from each other and may be any of the substituents defined hereinabove, with the proviso that $R^1$ is different from $R^6$ and/or $R^2$ is different from $R^5$. In Scheme 2, "Bn" is a benzyl group.

Reaction Scheme 3 illustrates the synthesis of the compounds of Formula I (a 1,14-dicarboxylate) via a "1+1+1" addition of pyrroles. Each of $R^1$ through $R^6$ is independent from each other and may be any of the substituents defined hereinabove, with the proviso that $R^1$ is different from $R^6$ or $R^2$ is different from $R^5$. In Scheme 3, "Bn" is a benzyl group, and "tBu" is tert-butyl.

REACTION SCHEME 1

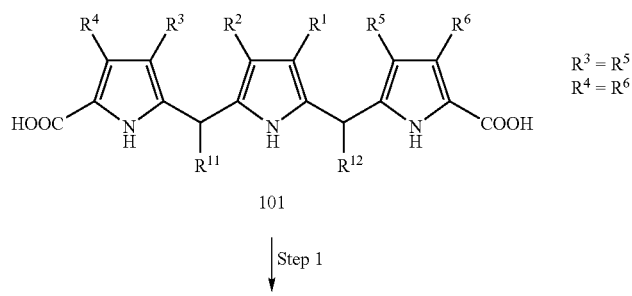

$R^3 = R^5$
$R^4 = R^6$

101

Step 1

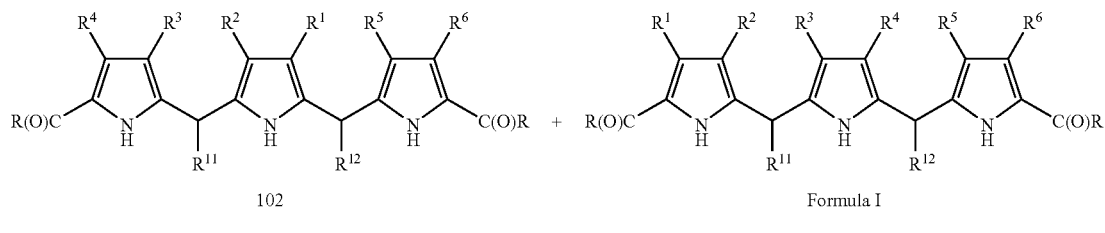

102          Formula I

Purification

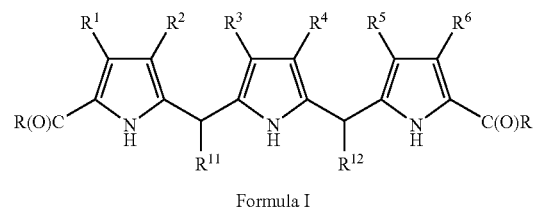

Formula I where R is hydrogen, alkyl, aryl, or aralkyl

As illustrated in Reaction Scheme 1, Step 1, the tripyrrane dicarboxylic acid of formula 101 is decarboxylated by treatment with trifluoroacetic acid at a temperature of about 20–50° C. This reaction is accompanied by rearrangement of Tripyrranes of formula 101 are known in the art or may be prepared by methods known in the art, as disclosed and described for example in the texaphyrin patents previously incorporated by reference herein.

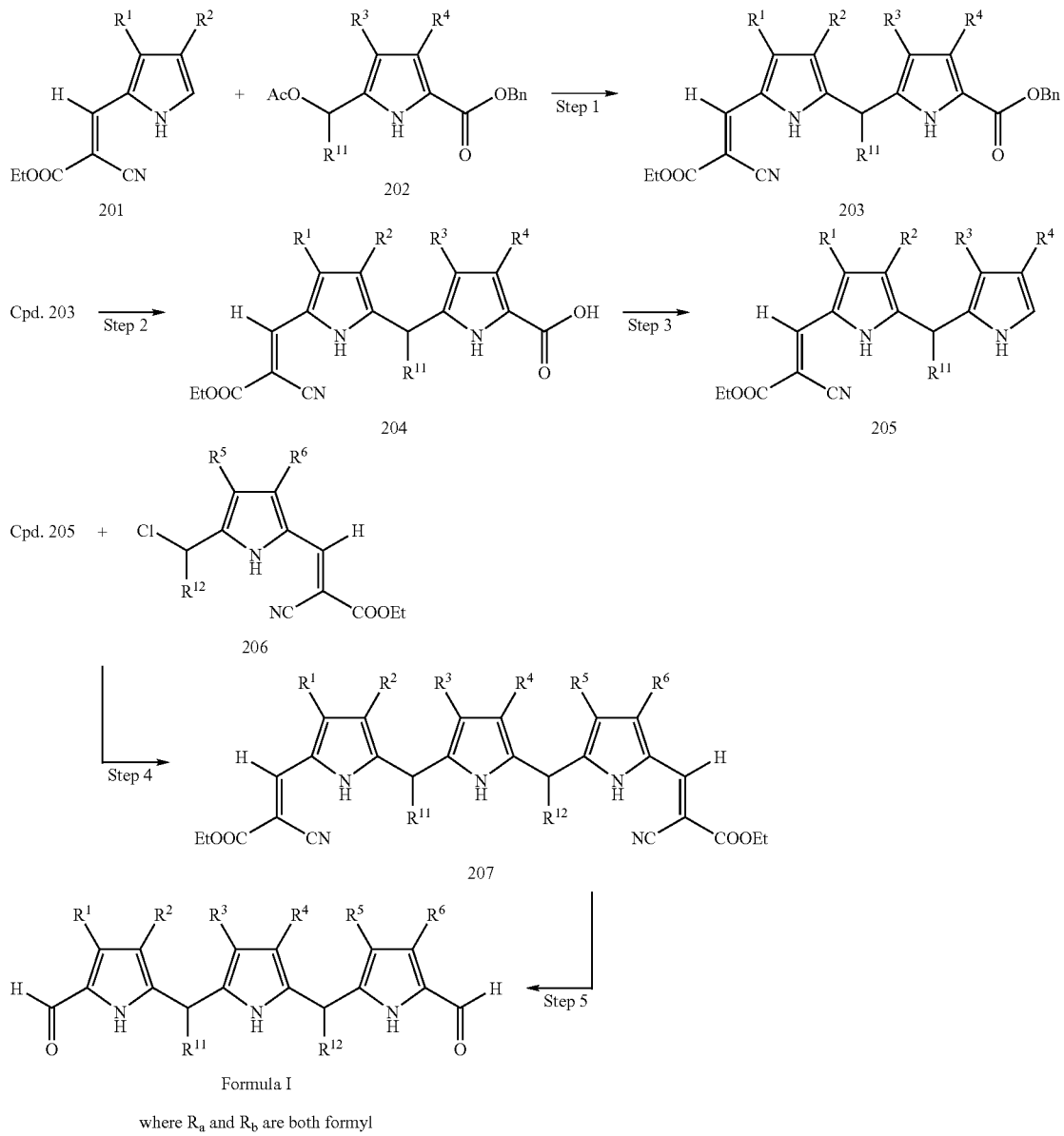

the tripyyrole to a mixture of intermediates, which upon reaction with a formylating agent, for example triethylorthoformate, yield the desired non-symmetric tripyrrane-1,14-dialdehyde of Formula I where R is hydrogen plus the equivalent symmetric tripyrranes-1,14-dialdehyde of formula 102. Similarly, reaction of the intermediate with triethylorthoacetate gives a similar mixture of tripyrranes in which R is methyl. The two isomeric tripyrranes are then separated and purified by methods known by those skilled in the art to give the desired product of Formula I where R is hydrogen, or where R is methyl.

As illustrated in Reaction Scheme 2, Step 1, an equimolar amount or a slight excess of a 2-(2-cyano 2-ethoxycarbonyl-ethen-1-yl)pyrrole derivative, shown as a compound of formula 201, is reacted with a 2-acetoxymethyl-5-benzyloxycarbonylpyrrole derivative of formula 202 in an organic solvent, preferably toluene, in the presence of a catalytic amount of p-toluenesulfonic acid to give the dipyrromethane of formula 203. The benzyl protecting group of the dipyrromethane 203 is then removed by palladium-catalyzedhydrogenation, as shown in Step 2, to give the corresponding dipyrromethane-2-carboxylate derivative of formula 204. As shown in Step 3, compound 204 is then decarboxylated in the presence of trifluoroacetic acid ("TFA") to form the unstable dipyrromethane of formula 205. This compound is then reacted in situ (Step 4) with ah excess amount of a 2-chloromethyl-5-(2-cyano 2-ethoxycarbonyl-ethen-1-yl)pyrrole of formula 206, in an organic solvent in the presence of a catalytic amount of tin(IV) chloride, to form the non-symmetric tripyrrane of formula 207. The ethylcyanoacrylate groups are then cleaved with alkali to give the non-symmetric tripyrrane α,α'-dialdehyde of Formula I.

Pyrroles of formula 201 may be prepared by first formylating a 3,4-substituted pyrrole at the 2-position by standard methods, such as reaction with phosphorous oxychloride/dimethylformamide complex. The resulting 2-formyl pyrrole is then protected by reaction with ethyl cyanoacetate to give compound 201.

Pyrroles of formula 202 may be prepared by methods known in the art, as disclosed and described in, for example, the texaphyrin patents previously incorporated by reference herein.

Pyrroles of formula 206 may be prepared by formylating a 2-methyl-3,4-optionally substituted pyrrole 5-carboxylate via standard methods to give the corresponding 5-formyl pyrrole, which is then reacted with ethyl cyanoacetate to give 5-(2-cyanoacrylic acid ethyl ester)-2-methylpyrrole. This is chlorinated by standard methods (for example, by reaction with sulfuryl chloride) to give the 2-chloromethylpyrrole of formula 206.

REACTION SCHEME 3

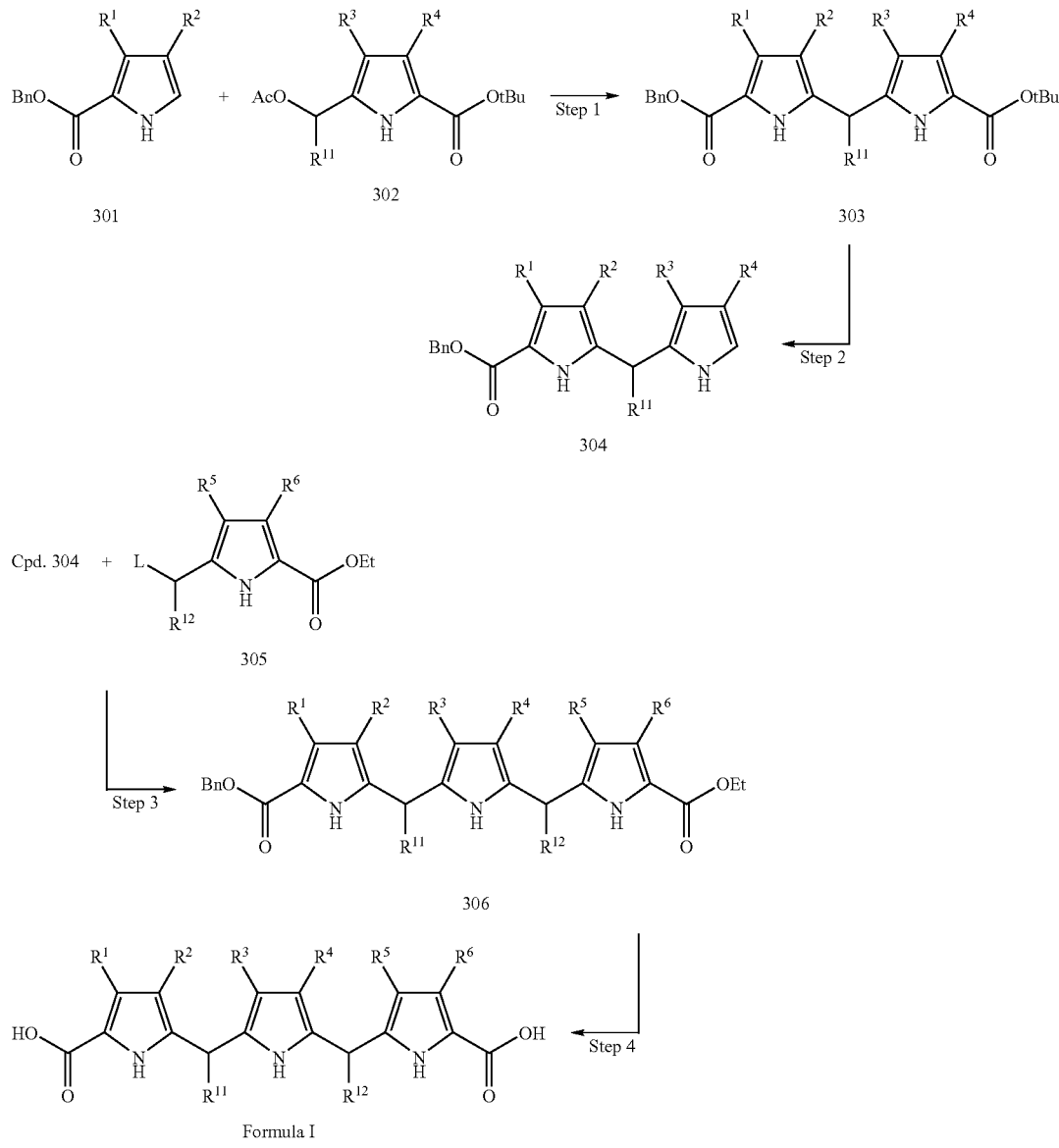

Formula I where $R_a$ and $R_b$ are both carboxy

As illustrated in Reaction Scheme 3, Step 1, an equimolar amount or a slight excess of a 2-benzyloxycarbonylpyrrole of formula 301 is reacted with a 2-acetoxymethyl-5-t-butyloxycarbonylpyrrole of formula 302 in an organic solvent with a catalytic amount of p-toluenesulfonic acid to give the dipyrromethane of formula 303. The t-butyloxycarbonyl group on the dipyrromethane is cleaved in the presence of acid in Step 2 to give the corresponding unstable dipyrromethane of formula 304, which is then reacted in situ (Step 3) with an excess amount of a 5-ethoxycarbonylpyrrole derivative of formula 305 (where L is a leaving group as defined herein, preferably chloro or bromo), in an organic solvent in the presence of an acid to form the non-symmetric α-benzyloxycarbonyl-α'-ethoxycarbonyl tripyrrane 306. In step 4 the benzyloxycarbonyl group is then cleaved by palladium-catalyzed hydrogenation, and the ethoxycarbonyl groups are hydrolysed with lithium hydroxide, to give the non-symmetric tripyrrane α,α'-dicarboxylate of Formula I where Ra and $R_b$ are both carboxyl.

Pyrroles of formula 301 are prepared by methods known in the art.

Pyrroles of formula 302 are prepared by methods known in the art, as disclosed and described in, for example, the texaphyrin patents previously incorporated by reference herein.

Pyrroles of formula 305 are prepared by methods known in the art.

Alternatively, the α,α'-dicarboxyltripyrrane of Formula I may be prepared by oxidizing the tripyrrane α,α'-dialdehyde, a compound of Formula I in which $R_a$ and $R_b$ are both formyl groups (from Scheme 2) with t-butyl hypochloride or $SOCl_2$ at moderately high temperatures.

The dicarboxylate of Formula I may be decarboxylated, if desired, by reaction with TFA to give the α-free tripyrrane of formula 308.

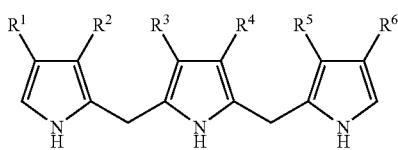

308

The unstable tripyrrane 308 may be reacted with triethyl orthoformate to give the corresponding 2,5-diformyl derivative, or with triethyl orthoacetate to give the 2,5-diacetyl derivative.

Presently Preferred Embodiments

Preferred among the non-symmetric tripyrranes of the invention of Formula I are those where each of $R^1$ through $R^6$, $R^{11}$ and $R^{12}$ is independently selected from hydrogen, optionally substituted alkyl (particularly hydroxyalkyl), optionally substituted alkoxy (particularly —$O(CH_2CH_2O)_x$ $CH_3$, where x is an integer of 1–20, preferably 1–10, and more preferably 2–5), and optionally substituted carboxyalkyl. In a more preferred embodiment, $R^1$, $R^2$, $R^4$ and $R^6$ are alkyl; $R^3$ and $R^5$ are hydroxyalkyl; $R^{11}$ and $R^{12}$ are hydrogen, and $R_a$ and $R_b$ are —CHO. More preferably, $R^1$ and $R^2$ are ethyl, $R^4$ and $R^6$ are methyl, and $R^3$ and $R^5$ are 3-hydroxypropyl.

Utility, Testing and Administration

General Utility

The compounds of Formula II of the present invention are effective in the treatment of conditions known to respond to metallotexaphyrin therapy, including diseases characterized by neoplastic tissue, (e.g. the cancers sarcoma, lymphoma, leukemia, carcinoma, brain metastases, glioma, glioblastoma, cancer of the prostate, melanoma, and the like), cardiovascular diseases (e.g., atherosclerosis, intimal hyperplasia and restenosis) and other activated macrophage-related disorders including autoimmune diseases (e.g., rheumatoid arthritis, Sjogrens, scleroderma, systemic lupus erythematosus, non-specific vasculitis, Kawasaki's disease, psoriasis, Type I diabetes, pemphigus vulgaris, multiple sclerosis), granulomatous diseases (e.g., tuberculosis, sarcoidosis, lymphomatoid granulomatosis, Wegener's granulomatosus), inflammatory diseases (e.g., inflammatory lung diseases such as interstitial pneumonitis and asthma, inflammatory bowel disease such as Crohn's disease, and inflammatory arthritis), viral diseases (in particular retroviruses and especially HIV and AIDS), transplant rejection (e.g., in heart/lung transplants) and in ophthalmic diseases that result from undesired neovascularization, in particular age-related macular degeneration.

Testing

Activity testing is conducted as described in those patents and patent applications incorporated by reference above.

Synthesis of Compounds of Formulae A and B, and other Macrocycles

The tripyrranes of Formula I can be used to prepare a wide variety of polypyrrolic macrocyclic compounds. In general, the preparation of substituted polypyrrolic macrocycles includes two steps: (a) an acid-catalyzed cyclization step, which can include the use of a cyclization agent, and (b) an oxidation step, which is optionally carried out concurrently with a metallation step, to form a fully conjugated macrocycle from the cyclized intermediate. A cyclization agent can be used in step (a) and, typically, is a Lewis acid or a Brønsted acid. At the conclusion of the cyclization reaction, a reaction mixture results, which may optionally be used directly in the oxidation step (b) without the intervening isolation or purification of the intermediate present in the reaction mixture. The oxidation of the cyclization reaction mixture to the desired macrocyclic compound can be accomplished by any of the usual oxidization agents generally known by those skilled in the art as suitable to accomplish this type of aromatization.

Alternative syntheses are described below with reference to Reaction Schemes 4 through 8.

Brief Description of Reaction Schemes

Reaction Scheme 4 illustrates a general synthesis of polypyrrolic macrocycles. A compound of Formula I where $R_a$ and $R_b$ are formyl groups is reacted, in the presence of an acid catalyst, with a planar cyclic co-reactant to form a cyclized intermediate, which is immediately oxidized to form the corresponding polypyrrolic macrocycle.

Reaction Scheme 5 illustrates a generalized synthesis of polypyrrolic macrocycles where a compound of Formula I where $R_a$ and $R_b$ are carboxylic acid is cyclized, in the presence of an acid catalyst, with a planar cyclic co-reactant to form a cyclized intermediate, which is immediately oxidized to form the corresponding porphyrin compound or other polypyrrolic macrocycle.

Reaction Scheme 6 illustrates the synthesis of a texaphyrin comprising the steps of: (a) cyclizing, in the presence of an acid catalyst, a compound of Formula I where $R_a$ and $R_b$ are functional groups, e.g. —CHO, with a 1,2-diaminobenzene to give a nonaromatic sp³ macrocycle; and b) mixing the nonaromatic sp³ macrocycle with a metal cation "M" and an oxidant to give a texaphyrin.

Reaction Scheme 7 illustrates the synthesis of a sapphyrin by condensing a compound of Formula I where $R_a$ and $R_b$ are functional groups, e.g. —CHO, with a bipyrrole diacid to give a sapphyrin.

Reaction Scheme 8 is an alternative process for synthesizing a sapphyrin, by condensing a compound of Formula I where $R_a$ and $R_b$ are carboxylic acid with a bipyrrole substituted at the α and α' positions with functional groups, e.g. —CHO, to give a sapphyrin.

REACTION SCHEME 4

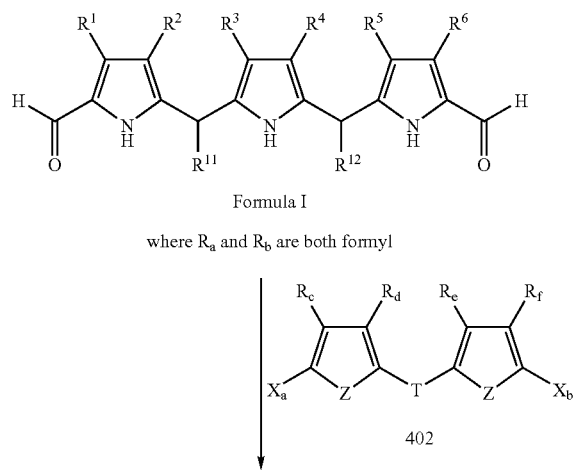

Formula I where $R_a$ and $R_b$ are both formyl

402

As illustrated in Reaction Scheme 4, an α,α'-dialdehyde tripyrrane of Formula I where $R_a$ and $R_b$ are both formyl groups, is reacted with an appropriately functionalized planar cyclic compound of formula 402, prepared according to methods known in the art. Simultaneous cyclization and oxidation takes place, in a suitable organic solvent, to give a polypyrrolic macrocycle of structure 403, and structural isomers thereof. The structural isomers are isolated conventionally, for example by HPLC.

In the above formulas, $R_c$–$R_f$ are independently hydrogen, lower alkyl, alcohol or carbonyl-containing groups. In presently preferred embodiments, $R_c$–$R_f$ are selected from the group consisting of hydrogen, methyl, ethyl, propyl, butyl, —$C_8H_{17}$, —$OCH_3$, —$CH_2OH$, —$(CH_2)_4OH$, —$O(CH_2)_3$ OH, —$(CH_2)_2COOH$, —$(CH_2)_2COOCH_3$, and —$(CH_2)_2$ $COOC_2H_5$. $X_a$ and $X_b$ are independently hydrogen or —COOH. T is a covalent bond, alkylene, pyrrolylene, furanylene, phenylene, thiophenylene, benzylene, or alkylene-pyrrolene-alkylene. Preferably, T is selected from the group consisting of a covalent bond, methylene, pyrrolene, furanylene, thiophenylene, benzylene and methylene-pyrrolene-methylene. Z is independently >NH, —O—, or —S—, preferably >NH.

Thus, a compound of formula 403 where Z is >NH at both occurrences, and T is a covalent bond, is a sapphyrin. A compound of formula 403 where Z is >NH at both occurrences, and T is methylene, is a pentaphyrin.

REACTION SCHEME 5

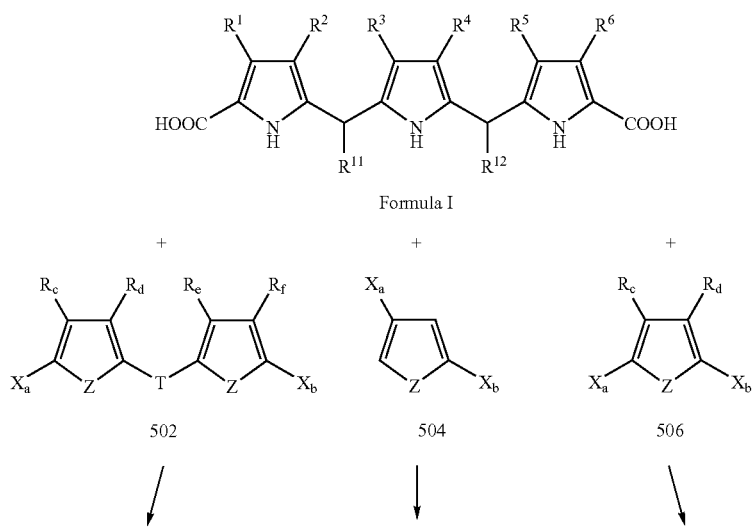

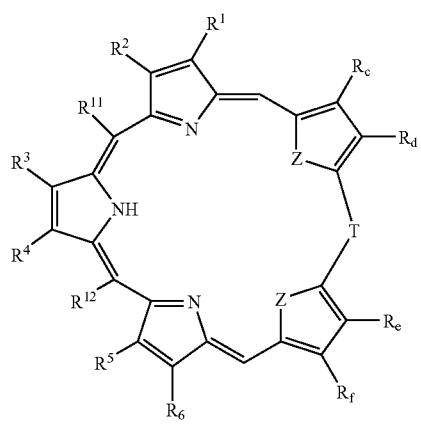
503

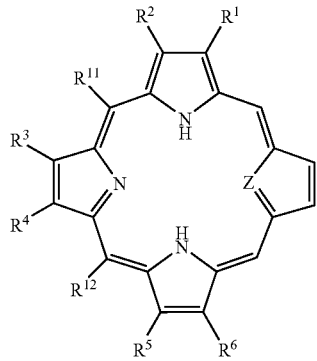
505

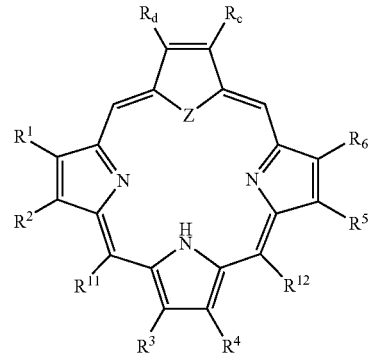
507

As illustrated in Reaction Scheme 5, a tripyrrane of Formula I where $R_a$ and $R_b$ are both carboxyl is reacted with an appropriately functionalized planar cyclic co-reactant 502, 504, or 506, prepared according to methods known in the art. Simultaneous cyclization and oxidation takes place, in a suitable organic solvent, to give a polypyrrolic macrocycle of structure 503, 505, or 507 and structural isomers of each. The structural isomers are isolated conventionally, for example by HPLC.

In the above formulas, $R_c$–$R_f$, Z and T are as described above under Reaction Scheme 4. $X_a$ and $X_b$ are groups capable of coupling with the unsubstituted α-positions of the terminal pyrrole rings of compound 502, typically —CHO or —CHR'-L where R' is hydrogen, alkyl such as methyl or ethyl, or aryl such as phenyl, pyridyl, or phenanthrenyl; and L is a leaving group. By "leaving group" is meant a moiety, such as iodo, bromo, chloro, tosylate, mesylate, —NH$_2$, —OH, or —OAc, that is readily lost or displaced under acid catalysis or nucleophilic attack to form a cationic intermediate, e.g., a "—CH$_2$$^+$" group or other groups, as disclosed in Dolphin, D, ed., The Porphyrins: Vol. 1, Structure and Synthesis, Part A, pp. 148, 167, Academic Press, NY, 1978. This cationic intermediate is then attached in a nucleophilic fashion to the α-position of the tripyrrane. In a preferred embodiment, $X_a$ and $X_b$ are selected from the group consisting of —CHO, —CH$_2$OAc, —CH$_2$NH$_2$, and —CH(Ar)-OAc where Ar is aryl having from 5 to 7 ring carbons, and Ac I acetyl.

REACTION SCHEME 6

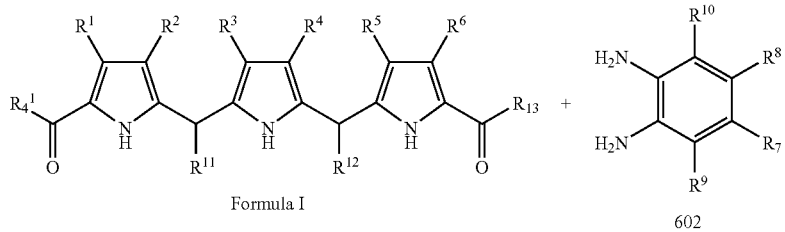
Formula I     602

Step 1

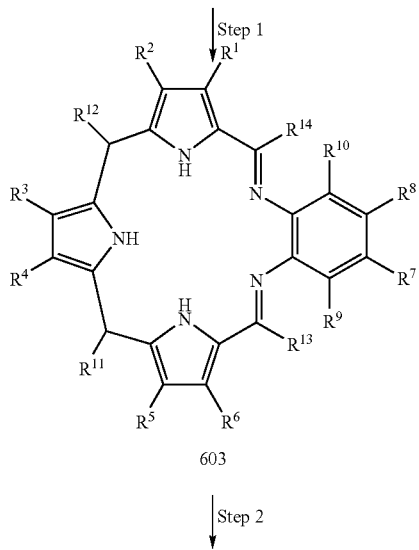
603

Step 2

-continued

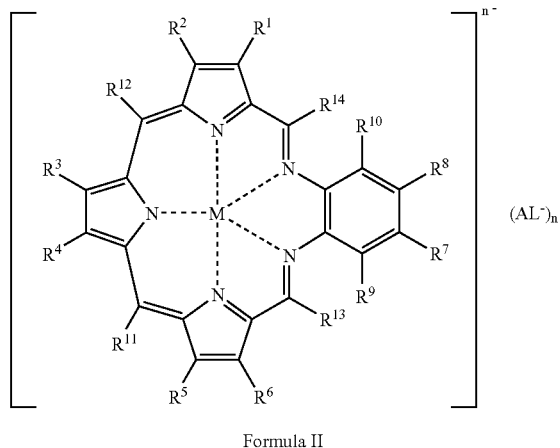

Formula II

As illustrated in Reaction Scheme 6, in Step 1 a tripyrrane of Formula I where each of $R_a$ and $R_b$ is an aldehyde is condensed with a 1,2-diaminobenzene of formula 602 to give a nonaromatic $sp^3$ hybridized macrocycle of formula 603. In Step 2, the macrocyclic intermediate 603 is simultaneously metallated and oxidized by mixing compound 603 with a metal salt $M^+(AL^-)_n$, a Brønsted base and an oxidant, with stirring at ambient temperature or heating at reflux for about 2 hours to about 24 hours, to give a texaphyrin of Formula II and structural isomers thereof. The structural isomers are isolated conventionally, for example by HPLC.

The metal cation is preferably in the form of a metal salt and the oxidant may be selected from, for example, air, oxygen, platinum oxide, chloranil and 2,3-dichloro-1,4-benzoquinone. The reaction takes place in an organic solvent that dissolves the nonaromatic macrocycle intermediate. This process is discussed in greater detail in the texaphyrin patents cited by reference previously herein.

Generally following the above Reaction Scheme 6, a tripyrrane of formula I can be reacted, for example, with a diaminomaleonitrile (605), a diaminonaphthalene 607, or a diaminophenanthrene 609, to give the corresponding macrocycles 606, 608, or 610, as shown schematically below. As would be clear to those skilled in the art, other diamino-substituted starting materials may be used to synthesize corresponding macrocycles, which may be converted to metal complexes as shown above.

REACTION SCHEME 6A

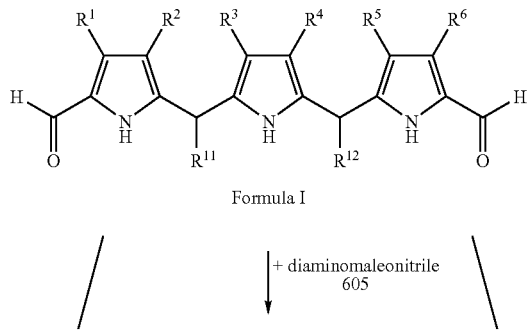

Formula I

+ diaminomaleonitrile
605

-continued
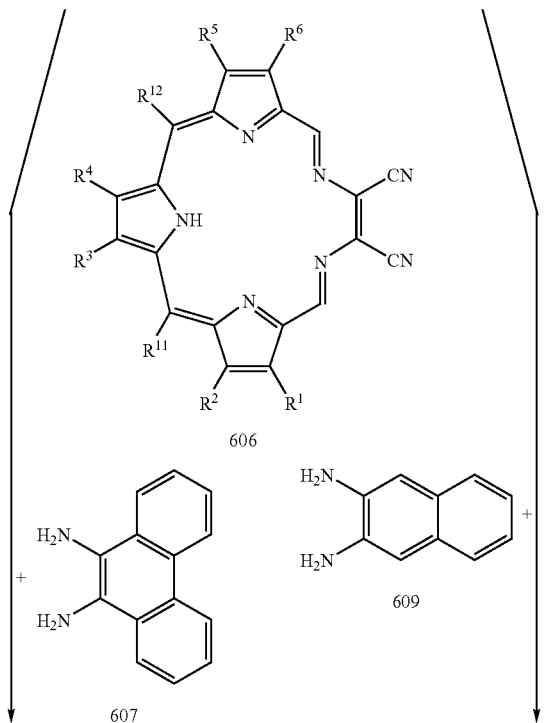
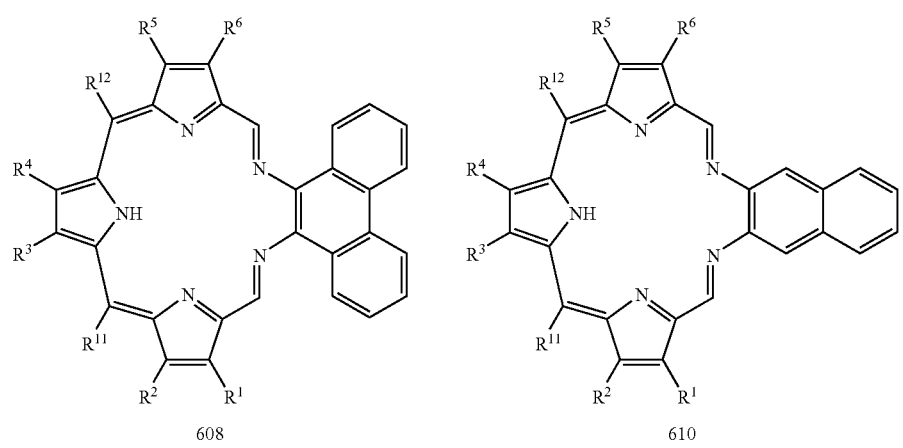

As illustrated in Reaction Scheme 7, a tripyrrane of Formula I (in which $R_a$ and $R_b$ are both formyl groups) is reacted with a bipyrrole diacid of formula 702, prepared according to methods known in the art, in a suitable organic solvent. Simultaneous cyclization and oxidation takes place, to give a sapphyrin of formula 703 and structural isomers thereof. The compound of formula 703 can be isolated by conventional methods, for example HPLC.

The above process is discussed in greater detail in the sapphyrin patents cited by reference previously herein.

REACTION SCHEME 7

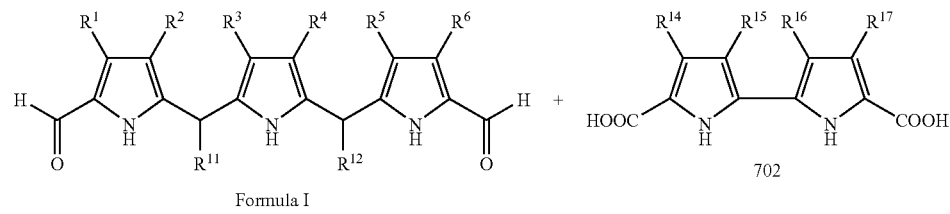

Formula I        702

Step 1

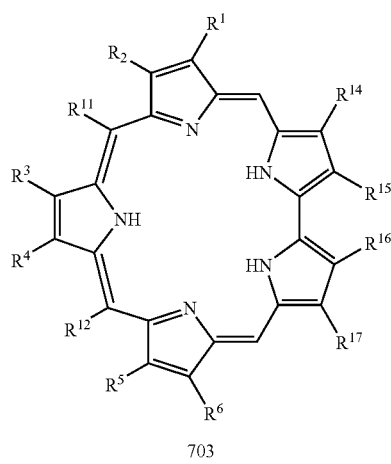

703

REACTION SCHEME 8

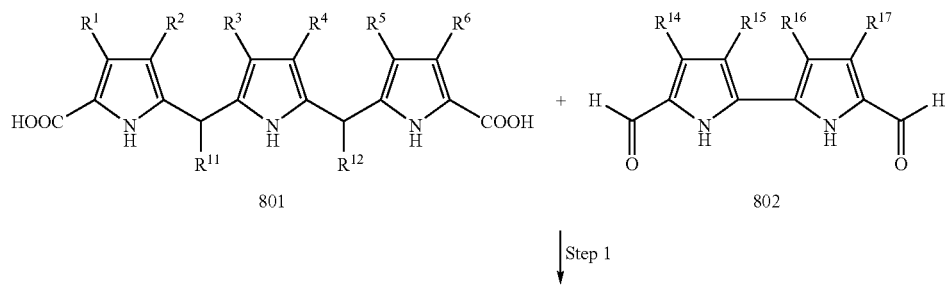

801        802

Step 1

-continued

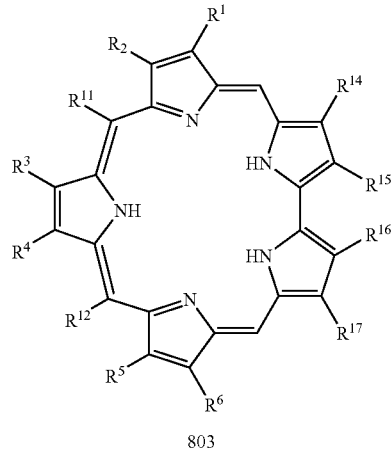

803

As illustrated in Reaction Scheme 8, a tripyrrane-1,14-dicarboxylic acid of formula 801 (alternatively, a tripyrrane where the 1,14-postions are hydrogen may be used) is reacted with a 2,2'-bis(formyl)-bipyrrole, a compound of formula 802, prepared according to methods known in the art. Simultaneous cyclization and oxidation takes place, in a suitable organic solvent, to give a sapphyrin of formula 803, and structural isomers thereof. This synthesis is described in greater detail in PCT Pubin. WO 97/32884 and in the sapphyrin patents incorporated by reference previously herein. The compound of formula 803, and if desired the structural isomers, may be isolated and purified conventionally, for example by HPLC.

Presently Preferred Embodiments

Of the texaphyrins of Formula II of the present invention, presently preferred are those where each of $R^1$ through $R^6$, $R^{11}$ and $R^{12}$ is selected from hydrogen, optionally substituted alkyl, optionally substituted alkoxy, carboxyl, and optionally substituted carboxyalkyl.

In another preferred embodiment, $R^1$, $R^2$, $R^4$ and $R^6$ are alkyl; $R^3$ and $R^5$ are hydroxyalkyl; $R^7$ and $R^8$ are hydrogen, hydroxy, optionally substituted alkyl, or optionally substituted alkoxy, and $R^9$, $R^{10}$, $R^{11}$ and $R^{12}$ are hydrogen. More preferably, $R^1$ and $R^2$ are ethyl, $R^4$ and $R^6$ are methyl, $R^3$ and $R^5$ are 3-hydroxypropyl, and $R^7$ and $R^8$ are independently chosen from hydrogen, hydroxy, methyl, methoxy., —OCH$_2$CH$_2$CH$_2$OH, and —O(CH$_2$CH$_2$O)$_3$CH$_3$. In yet another preferred embodiment, $R^1$, $R^2$, $R^4$ and $R^6$ are optionally substituted alkyl; $R^3$ and $R^5$ are hydroxyalkyl; $R^7$ is hydrogen, hydroxy, optionally substituted alkyl, or optionally substituted alkoxy, $R^8$ is a site-directing molecule or a chemotherapeutic agent; and $R^9$, $R^{10}$, $R^{11}$ and $R^{12}$ are hydrogen.

Of the sapphyrins of Formula III of the present invention, presently preferred are those where each of $R^1$ through $R^6$, $R^{11}$ and $R^{12}$ is selected from hydrogen, optionally substituted alkyl, optionally substituted alkoxy, carboxyl, and optionally substituted carboxyalkyl.

In a more preferred embodiment, $R^1$, $R^2$, $R^4$ and $R^6$ are alkyl; $R^3$ and $R^5$ are hydroxyalkyl; $R^{11}$ and $R^{12}$ are hydrogen; and $R^{14}$, $R^{15}$, $R^{16}$ and $R^{17}$ are alkyl. More preferably, $R^1$ and $R^2$ are ethyl, $R^4$ and $R^6$ are methyl, $R^3$ and $R^5$ are hydroxypropyl, $R^{14}$ and $R^{17}$ are ethyl, and $R^{15}$ and $R^{16}$ are methyl or ethyl.

REACTION SCHEME 9

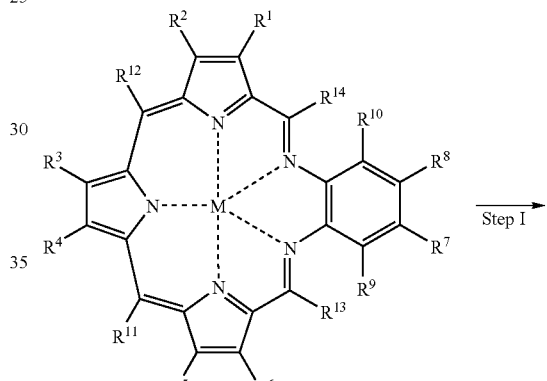

Formula II

900 where, for example $R^5$ represents
CH$_2$CH$_2$CH$_2$OH

Formula II

901 where, for example $R^5$ represents
2-Prop-1-yl-isoindole-1,3-dione

Formula II

903 where, for example $R^5$ represents
CH$_2$CH$_2$CH$_2$NH$_2$

Scheme 9

Step I

A compound of Formula II (compound 900, 1 eq.), triphenyl phosphine (6 eq.), phthalimide (6 eq.) and methylene chloride were mixed in a dry reaction flask. The reaction mixture was agitated for about five minutes at a temperature of about 0° C. To the agitating reaction mixture then was added diethyl azo dicarboxylate (DEAD, 6 eq.) and the resulting reaction mixture was agitated for about 4 hours at about 0° C. The progress of the reaction was checked by thin layer chromatography (TLC). The reaction mixture was stored at about −20° C. for about 10 hours after the TLC analysis showed the disappearance of the starting compound 900 and the appearance of the new compound 901.

Step II

The reaction mixture from Step I, above, was warmed to ambient temperature and then was mixed with methanol, and an excess of methyl amine (4% solution in methanol). The resulting reaction mixture was agitated for about an hour at ambient temperature. Progress of the reaction was monitored by TLC with the disappearance of compound 901 indicating the formation of compound 903.

The reaction mixture was concentrated under reduced pressure to yield a residue. The residue was diluted with 1M aqueous ammonium acetate buffer (pH of about 4.3) and the aqueous mixture then was extracted with methylene chloride. The methylene chloride layer was isolated and then washed (×2) with aqueous ammonium acetate buffer solution. The combined buffer layers were desalted by loading on a Sep-Pak column. The column is pretreated with methanol and buffer. The eluant used was 20–35% methanol in 33 mM acetate buffer. The desired compound (compound of Formula II where one or both $R^2$ and $R^5$ represent an amine group) usually separates as a colored band. The appropriate fractions were combined and concentrated under reduced pressure to yield a thick aqueous residue. This residue was once again loaded on a Sep-Pak column and eluted with methanol. The appropriate fractions were collected and concentrated under reduced pressure followed by drying for about 12 hours under reduced pressure to yield a compound of Formula II.

The following examples are provided to illustrate the practice of the present invention, and are intended neither to define nor to limit the scope of the invention in any manner.

EXAMPLE 1

Preparation of a Compound of Formula I

Preparation of a Compound of Formula I in which $R^1$ and $R^2$ are Ethyl, $R^4$ and $R^6$ are Methyl, $R^3$ and $R^5$ are 3-Hydroxypropyl, $R^{11}$ and $R^{12}$ are Hydrogen, and $R_a$ and $R_b$ are both Formyl Method 1: Acid-catalyzed Rearrangement (Reaction Scheme 1)

7,8-Diethyl-3,12-bis(3-hydroxypropyl)-2,13-dimethyltripyrrane 1,14-dicarboxylic acid, a compound of formula 101 (5.1 g, 10.0 mmole), was dissolved in trifluoroacetic acid (16.5 mL) under a nitrogen atmosphere and heated to 35° C. for 2.5 hours. The solution was cooled to −20° C. and triethyl orthoformate (16.5 mL) added. The solution was stirred for 1 hour, then allowed to warm to 0° C. Water (33 mL) was added to the solution, causing the precipitation of a pale red solid, which was filtered off and dried under vacuum to give a mixture of 7,8-diethyl-1,14-diformyl-3, 12-bis(3-trifluoroacetoxypropyl)-2,13-dimethyltripyrrane and 2,3-diethyl-1,14-diformyl-7,12-bis(3-trifluoroacetoxypropyl)-8,13-dimethyltripyrrane in 49% yield.

The mixture of isomers dissolved in methanol (153 mL). Lithium hydroxide (1.6 g) in water (16 mL) was added to the solution, and the mixture refluxed for two hours and cooled to room temperature. Water (75 mL) was added, and the methanol was removed under reduced pressure, precipitating a dark solid. The solid was filtered and dried affording a mixture of 7,8-diethyl-1,14-diformyl-3, 12-bis(3-hydroxypropyl)-2,13-dimethyltripyrrane (a compound of formula 102) and 2,3-diethyl-1,14-diformyl-7,12-bis(3-hydroxypropyl)-8,13-dimethyltripyrrane (a compound of Formula I) in 80% yield.

The mixture of isomeric tripyrranes was separated by first converting to the corresponding diacetoxytripyrranes 7,8-diethyl-1,14-diformyl-3,12-bis(3-acetoxypropyl)-2,13-dimethyltripyrrane and 2,3-diethyl-1,14-diformyl-7,12-bis(3-acetoxypropyl)-8,13-dimethyltripyrrane by dissolving the solids (2.67 g), together with N,N-dimethylaminopyridine (2.9 mg), in tetrahydrofuran (50 mL). Triethylamine (5 mL) and acetic anhydride (2.5 mL) were added to the reaction mixture and allowed to stir for 4 hrs. The solvent was removed under reduced pressure and the resulting oil was redissolved in dichloromethane (40 mL), washed with water, dried with magnesium sulfate and filtered. The solvent was removed under reduced pressure and dried overnight under vacuum. The mixture of isomeric diacetoxy tripyrranes was partially purified by multiple recrystallization from dichloromethane/ethanol. The enriched tripyrrane was then purified via semi-preparative HPLC, to give about 10 mg of pure 2,3-diethyl-1,14-diformyl-7,12-bis(3-acetoxypropyl)-8,13-dimethyltripyrrane.

Similarly, following the acid-catalyzed rearrangement of Method 1, and starting with the following compounds of formula 101 in which $R^{11}$ and $R^{12}$ are hydrogen:

| $R^1$ | $R^2$ | $R^3$ and $R^5$ | $R^4$ and $R^6$ |
|---|---|---|---|
| Et | Me | 2-HO—Et | Me |
| Et | F | Ph | cyclohexyl |
| Pr | Pr | 4-HO—Bu | 2-F—Et |
| Et | CH=CH$_2$ | 3-MeO—Pr | Me |
| H | OH | MeO | cyclopropyl |
| PhCH$_2$ | H | PrO | Et |
| Me—C(O) | H | Et | Hexyl |
| NO$_2$ | H | 3-HO—PrO | Me |
| 1-Imidazolyl | H | Cl | Pr | the corresponding compounds of Formula I are obtained:

| $R^1$ | $R^2$ | $R^3$ and $R^5$ | $R^4$ and $R^6$ |
|---|---|---|---|
| Et | Me | 2-AcO—Et | Me |
| Et | F | Ph | cyclohexyl |
| Pr | Pr | 4-AcO—Bu | 2-F—Et |
| Et | CH=CH$_2$ | 3-MeO—Pr | Me |
| H | Oac | MeO | cyclopropyl |
| PhCH$_2$ | H | PrO | Et |
| Me—C(O) | H | Et | Hexyl |
| NO$_2$ | H | 3-AcO—PrO | Me |
| 1-Imidazolyl | H | Cl | Pr | in which Me is methyl, Et is ethyl, Pr is propyl, Bu is butyl, Ac is acetyl, and Ph is phenyl.

Method 2: "1+1+1" Addition Synthesis

A. Preparation of 2-cyano-3-(3,4-diethyl-1H-pyrrol-2-yl) acrylic acid ethyl ester, a Compound of Formula 201 where $R^1$ and $R^2$ are both Ethyl

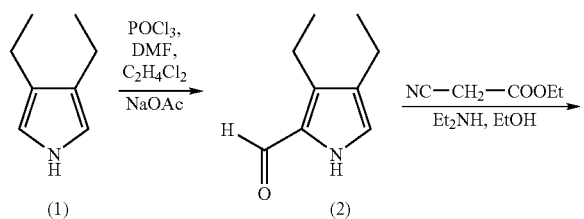

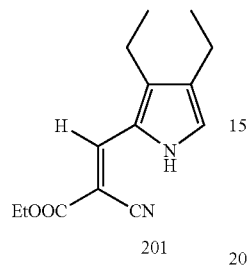

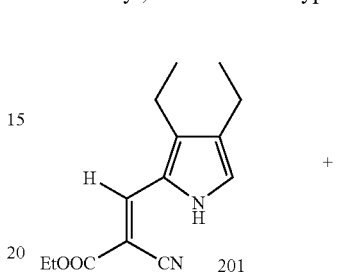

Phosphorous oxychloride (25 mL) was purified by distillation at atmospheric pressure in a short-path distillation apparatus over P$_2$O$_5$; the fraction boiling between 105–108° C. was retained. 3,4-Diethylpyrrole, the compound of formula (1) (26.0 g) was purified by distillation in a short-path distillation apparatus at 0.3–0.5 mm Hg vacuum. 16.2 Grams of an oil was recovered.

Dimethylformamide (DMF) (11.2 mL, 144.5 mmol) was cooled to 10° C. in an ice bath, and the purified phosphorous oxychloride (18.5 mL, 144.5 mmol) was added over 15 minutes, while maintaining the temperature between 10 and 20° C. The ice bath was removed and the solidified complex was allowed to warm to room temperature. Dichloroethane (10 mL) was added to the solid, which was heated to 30° C. to facilitate dissolution. The mixture was stirred for 10 minutes while additional dichloroethane (23 mL) was added, and the resulting solution was cooled in an ice bath. 3,4-Diethylpyrrole (16.2 g, 131.4 mmol) was dissolved in 33 mL of dichloroethane and added dropwise over the course of 30 minutes to the cooled solution, with vigorous stirring. The ice bath was then removed, and the solution was heated to reflux and stirred at reflux for 10 minutes, after which it was cooled to room temperature. Sodium acetate (64.9 g, 790.9 mmol) dissolved in deionized water (133 mL) was added to the resulting reaction mixture while maintaining the temperature of the reaction below 30° C. The resulting two-part mixture was heated to reflux while maintaining vigorous stirring. The mixture, which had become deep brown upon addition of pyrrole, now turned dark magenta. The mixture was stirred at reflux for 15 minutes. Upon cooling to room temperature, the mixture was separated, and the combined organic layers were washed (3×) with sodium bicarbonate solution (50 mL), dried, and filtered, and the solvent was removed under reduced pressure. The resulting oil was dried overnight under vacuum to give 3,4-diethyl-2-formylpyrrole, the compound of formula (2), in 70.9% yield.

The 3,4-diethyl-2-formylpyrrole (14.1 g, 93.1 mmol) was dissolved in 200 mL of dry ethanol, and ethyl cyanoacetate (20 mL, 137.9 mmol) and diethylamine (20 mL, 193.3 mmol) were added to the solution. The reaction mixture was heated to reflux under an inert atmosphere and stirred under reflux for 2 hours, after which it was cooled to room temperature and then placed in an ice bath. The resulting dark suspension was filtered through a medium filter, and the light brown solids were washed with cold ethanol. The collected filtrates were concentrated under reduced pressure, precipitating more solids. The thick suspension was filtered, and the combined solids were separated and purified to give 2-cyano-3-(3,4-diethyl -1H-pyrrol-2-yl) acrylic acid ethyl ester, a compound of formula 201 in which R$^1$ and R$^2$ are both ethyl.

B. Preparation of 7-(3-acetoxypropyl)-1-(2-cyanoacrylic acid ethyl ester)-2,3-diethyl-8-methyldipyrrane-9-carboxylic acid (a Compound of Formula 204 in which R$^1$ and R$^2$ are both Ethyl, R$^3$ is 3-Acetoxypropyl, and R$^4$ is Methyl)

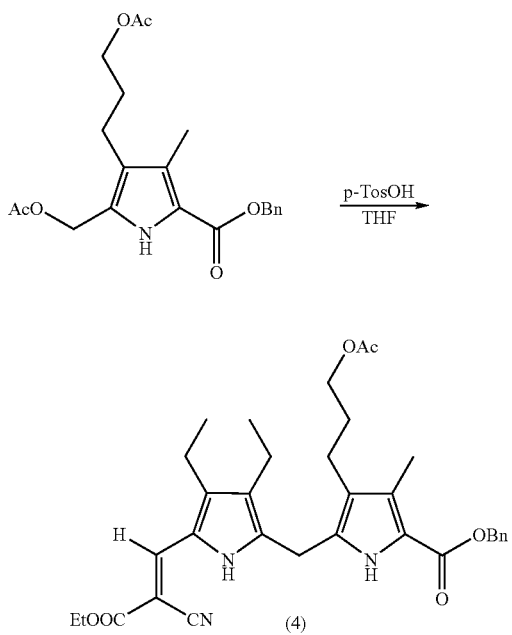

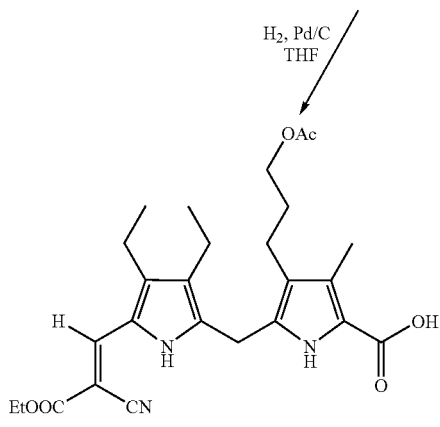

A mixture of 5-acetoxymethyl-4-(3-acetoxypropyl)-3-methyl-1H-pyrrole-2-carboxylic acid benzyl ester, a compound of formula (3) (1.8 g, 4.6 mmol), and 2-cyano-3-(3,4-diethyl-1H-pyrrol-2-yl) acrylic acid ethyl ester, a compound of formula 201 (1.2 g, 5.1 mmol), were dissolved in 50 mL of dry toluene. A catalytic amount of p-toluenesulfonic acid (0.03 g, 0.13 mmol) was added to the solution, diethyl-8-methyldipyrrane-9-carboxylic acid as a bright yellow solid (1.89 g, 81.7% yield), a compound of formula 204 in which $R^1$ and $R^2$ are both ethyl, $R^3$ is 3-acetoxypropyl, and $R^4$ is methyl.

C. Preparation of 4-(3-acetoxypropyl)-5-chloromethyl-2-(2-cyano 2-ethoxycarbonyl-ethen-1-yl)-3-methylpyrrole, a Compound of Formula 206 in which $R^5$ is 3-acetoxypropyl and $R^6$ is Methyl

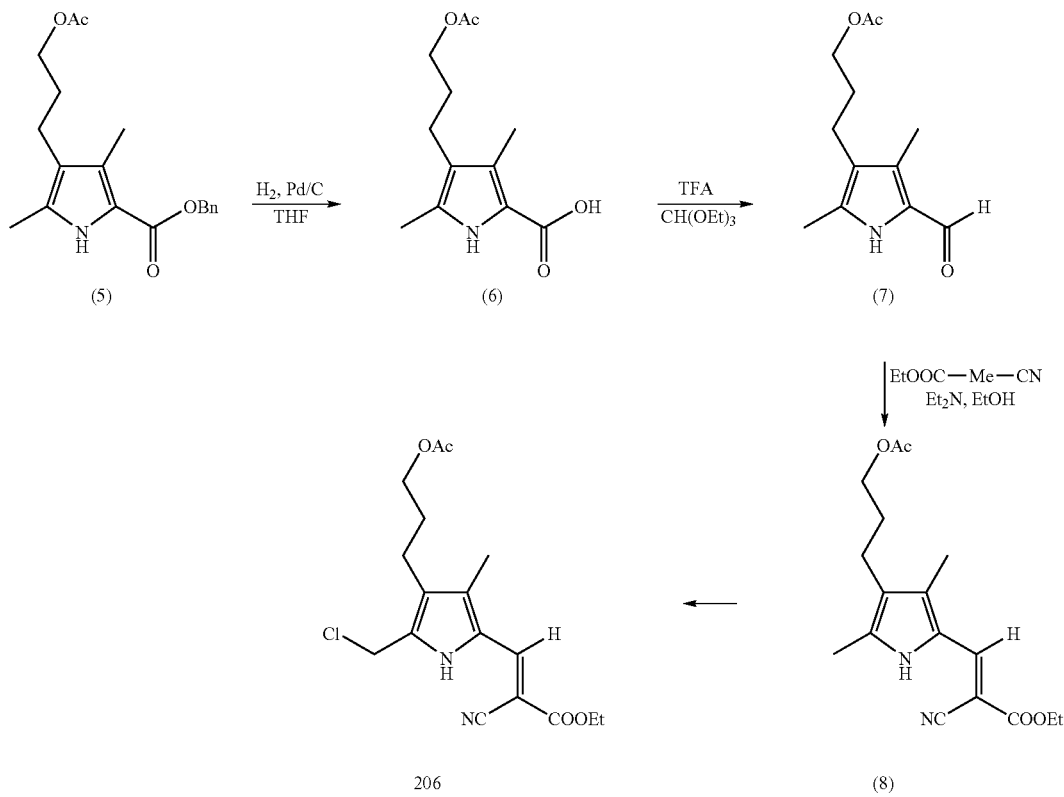

and the reaction mixture was heated to reflux under $N_2$ and stirred under reflux overnight. The resulting solution was washed with saturated sodium bicarbonate and saturated sodium chloride solutions, and the organic layer was separated out, dried, and filtered. The solvent was removed under reduced pressure to give a red oil, which was dried overnight and recrystallized from ethanol, to give 7-(3-acetoxypropyl)-1-(2-cyanoacrylic acid ethyl ester)-2,3-diethyl-8-methyldipyrrane-9-carboxylic acid benzyl ester, a compound of formula (4).

This compound (2.75 g, 4.8 mmol) was then dissolved in dry THF (100 mL), and 10% palladium on carbon (0.25 g) was added to the solution. The reaction mixture was placed under a nitrogen atmosphere, and the reaction flask was then evacuated and backfilled with hydrogen gas (4x). The reaction mixture was allowed to stir overnight under a hydrogen atmosphere. The suspension was then filtered to remove the palladium/carbon, and the resulting solution was concentrated under reduced pressure until solid began to fall out of solution. A small amount of THF was added to redissolve the solids, after which hexanes were added dropwise, causing a yellow solid to precipitate. The solids were filtered, rinsed with hexanes, and dried overnight under vacuum. to give 7-(3-acetoxypropyl)-1-(2-cyanoacrylic acid ethyl ester)-2,3-

4-(3-Acetoxypropyl)-3,5-dimethylpyrrole-2-carboxylic acid benzyl ester, the compound of formula (5) (18.6 g, 56.6 mmol), was dissolved in dry THF (440 mL), and 10% palladium on carbon (1.3 g) was added to the solution under a nitrogen stream. The reaction flask was evacuated until the solvent began to boil, and it was then backfilled with nitrogen (3x). The reaction flask was again evacuated until the solvent began to boil and was backfilled with hydrogen gas (5x). The reaction was then allowed to stir under hydrogen gas overnight. The resulting suspension was filtered to remove the palladium/carbon, and THF was added to redissolve the solids. Most of the THF was evaporated off, after which hexanes were added dropwise, with stirring, to the solution, causing a white solid to precipitate out. The solids were filtered, rinsed with hexanes, and dried overnight under vacuum to give 4-(3-acetoxypropyl)-3,5-dimethylpyrrole-2-carboxylic acid, the compound of formula (6) as a white crystalline powder (12.8 g, 94.2% yield). This compound (12.1 g, 50.2 mmol) was slurried in triethylorthoformate (60 mL), and the slurry cooled to 0° C. in an ice/brine bath. Trifluoroacetic acid (60 mL) was added while main taining the temperature under 5° C. The resulting solution was stirred for 1 hr, after which water (100 mL) and methylene chloride (100 mL) were added. The mixture was separated, and the organic layer was washed twice with 100 mL water, three times with 100 mL of saturated sodium bicarbonate, and once more with 100 mL of water to neutralize the mixture. The organic layer was then separated cyanoacrylic acid ethyl ester)-3-methylpyrrole as a fluffy yellow solid (1.57 g, 44.5% yield), a compound of Formula 206 in which $R^5$ is 3-acetoxypropyl and $R^6$ is methyl.

D. Preparation of 2,3-Diethyl-1,14-diformyl-7,12-bis-(3-hydroxypropyl)-8,13-dimethyltripyrane (a Compound of Formula 207 where $R^1$ and $R^2$ are both Ethyl, $R^3$ and $R^5$ are both 3-Hydroxypropyl, $R^4$ and $R^6$ are both Methyl

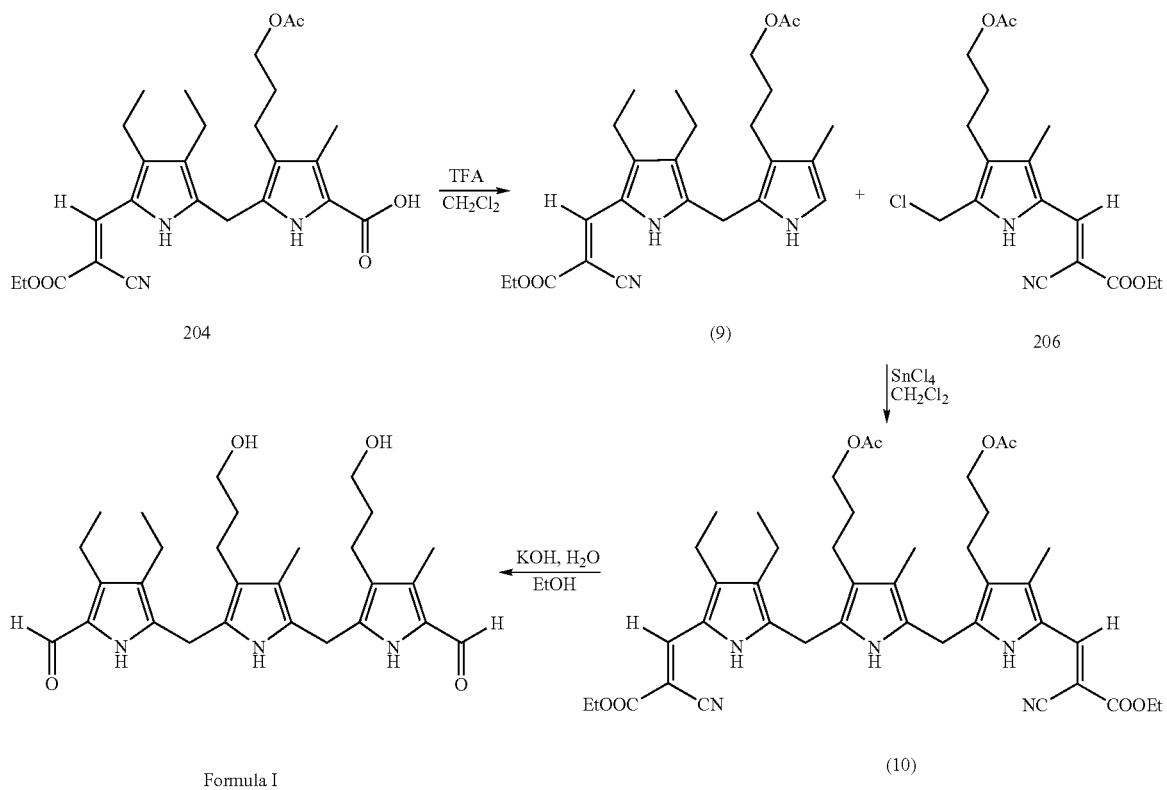

and dried, filtered and the solvent was removed from the filtrate under reduced pressure to give an oil. The oil was dried under vacuum overnight, to give crude 4-(3-acetoxypropyl)-3,5-dimethyl)-2-formylpyrrole, the compound of formula (7) as a solid.

To this formylpyrrole (9.4 g, 42.2 mmol) was added ethanol (150 mL), diethylamine (9.4 mL, 90.9 mmol) and ethyl cyanoacetate (9.4 mL, 88.8 mmol), and the mixture was heated to reflux to dissolve the solids. The resulting solution was stirred at reflux for 4 hours, then cooled to room temperature, and then to −10° C., causing the product to precipitate out of solution. The solids were filtered, washed twice with cold ethanol, and dried overnight under vacuum to give 4-(3-acetoxypropyl)-2-(2-cyano 2-ethoxycarbonyl-ethen-1-yl)-3,5-dimethylpyrrole as bright yellow fluffy crystals, the compound of formula (8), (10.3 g, 76.9% yield).

This compound was then chlorinated by dissolving 3.2 g (20 mmol) of the compound in dry methylene chloride (30 mL) and adding sulfuryl chloride (10.0 mL, 10.0 mmol) in methylene chloride dropwise, via syringe. The reaction was concentrated under reduced pressure until the product began to precipitate out, after which the mixture was diluted with 50 mL of diethyl ether. The precipitated solids were filtered, washed with diethyl ether, and dried for 4 hours under vacuum to give 4-(3-acetoxypropyl)-5-chloromethyl-2-(2-

The compound of formula 204 (0.48 g, 1.0 mmol; from Method 2B above) was suspended in dry methylene chloride (20 mL), the suspension was cooled to 5° C., and dry trifluoroacetic acid (0.50 mL) added. The resulting solution was stirred for 1 hour under $N_2$ at 5° C. 1M Tin(IV) chloride (50 µL, 0.05 mmol, 0.05 eq.) was added via syringe to the reaction mixture, after which the chloromethylpyrrole, the compound of formula 206 (0.39 g, 1.1 mmol; from Method 2C above), dissolved in methylene chloride (20 mL), was added. The reaction was stirred for 2 hours and then was quenched with 25 mL of water. The organic layer was separated and washed twice with 20 mL water. The solution was dried, solvent removed under reduced pressure, and the residue dried overnight. The resulting red solids were purified by chromatography or recrystallized from ethanol, evaporated under reduced pressure, and dried overnight under vacuum to give 2,3-diethyl-1,14-bis-[2-(2-cyanoacrylic acid ethyl ester)]-7,12-bis(3-acetoxypropyl)-8,13-dimethyltripyrrane, the compound of formula (10), as an orange solid (0.29 g, 38.4% yield).

E. Preparation of 2,3-Diethyl-1,14-diformyl-7,12-bis(3-hydroxypropyl)-8,13-dimethyltripyrane (a Compound of Formula I where $R^1$ and $R^2$ are both Ethyl, $R^3$ and $R^5$ are both 3-Hydroxypropyl, $R^4$ and $R^6$ are both Methyl, and $R_a$ and $R_b$ are both Formyl The compound of formula (10) (from D above) was then deprotected by adding ethanol (25 mL) to 0.5 g (0.7 mmol) of product, followed by addition of potassium hydroxide (2.6 g, 46.1 mmol) dissolved in deionized water (5 mL). The resulting solution was heated to reflux and stirred at reflux under nitrogen for 4.5 hours. The solution was cooled to room temperature and then to 0° C., after which deionized water (50 mL) was added dropwise over the course of 15 minutes. The volume of solvent was reduced under reduced pressure, and the remaining oil was dissolved in dichloromethane. The solvent was removed under reduced pressure and the oil was dried overnight under vacuum to give 2,3-diethyl-1,14-diformyl-7,12-bis-(3-hydroxypropyl)-8,13-dimethyltripyrrane as a brown solid (0.32 g, 97.6% yield), a compound of Formula I in which $R^1$ and $R^2$ are both ethyl, $R^3$ and $R^5$ are both 3-hydroxypropyl, $R^4$ and $R^6$ are both methyl, and $R_a$ and $R_b$ are both formyl.

Preparation of Other Compounds of Formula I

Other compounds of Formula I are prepared by:

optionally replacing 3-ethyl and 4-ethyl in the compound of formula (1) with other definitions of $R^1$ and $R^2$; and optionally replacing 3-methyl and 4-(3-acetoxypropyl) in the compound of formula (3) with other definitions of $R^3$ and $R^4$; and optionally replacing 3-methyl and 4-(3-acetoxypropyl) in the compound of formula 206 with other definitions of $R^5$ and $R^6$, and following the procedures of A, B, C, D, and E above, other compounds of Formula I are made.

For example, if:

compound (1) is replaced with 3-methyl-4-hydroxypyrrole;

compound (3) is replaced by 5-(acetoxymethyl)-4-(2-acetoxyethyl)-3-isopropyl-1H-pyrrole-2-carboxylic acid benzyl ester; and compound 206 is replaced by 4-(3-fluoropropyl)-5-chloromethyl-2-(2-cyanoacrylic acid ethyl ester)-3-cyclohexylpyrrole;

and the procedures of A, B, C, D, and E above are followed, the following compound of Formula I is made:

7-(2-acetoxyethyl)-13-cyclohexyl-14-diformyl-12-(3-fluoropropyl)-3-hydroxy-2-methyl-8-n-propyl-dimethyltripyrrane.

Similarly, the following compounds of Formula I in which $R^1$ and $R^{12}$ are hydrogen are prepared by choosing appropriately substituted compounds of formula (1), (3) and (206), and following the procedures of A, B, C, D, and E above.

| $R^1$ | $R^2$ | $R^3$ | $R^4$ | $R^5$ | $R^6$ |
|---|---|---|---|---|---|
| Et | Me | 2-HOEt | OH | 3-HOPr | F |
| F | n-Pr | cyclohexyl | MeO | EtO | CH=CH$^2$ |
| 4-HO—Bu | Me | Et | Me | Cl | cyclopropyl |
| OAc | MeC(O) | tert-Bu | EtO | F | 3-HOPr |
| O-n-Hexyl | Et | 4-HOBu | Me | Ph | Ph |
| Me | Me | 3-HOPr | nitro | Ph | 4-F—Ph |
| Ft | n-Pr | EtO | C(O)CH$_3$ | Me | 4-MeO—Ph |
| n-Pr | i-Pr | Cl | CH$_2$OH | Et | cyclohexyl |
| i-Pr | MeO | F | 2-HOEt | n-Pr | cyclopropyl |
| CH=CHCH$_3$ | EtO | Me | 2-HOPr | MeO | Me |
| n-Bu | NMe$_2$ | Et | cyclopropyl | EtO | MeO |
| n-pentyl | CH$_2$OH | n-Pr | cyclobutyl | N—PrO | EtO |
| NMe$_2$ | 2-HOEt | i-Pr | cyclopentyl | CH$_2$OH | n-PrO |
| Et$_2$NCH$_2$ | Ph | n-Bu | cyclohexyl | 2-HOEt | C(O)CH$_3$ |
| PhCH$_2$ | CH$_2$Ph | sec-Bu | Me | Ph | C(O)Et |
| PhCH$_2$CH$_2$ | 4-MeO—Ph | t-Bu | Me | CH$_2$Ph | 2-HOET |
| 4-F—Ph | 1-naphth | n-pentyl | Me | CH$_2$CH$_2$Ph | 3-HOPr |
| Imidazole | OH | isopentyl | Me | (CH$_2$)$_3$Ph | CH=CH$_2$ |
| Ph | MeO | n-decyl | Me | 3-NO$_2$—Ph | CH=CHCH$_3$ | in which Me is methyl, Et is ethyl, Pr is propyl, Bu is butyl, Ac is acetyl, and Ph is phenyl.
EXAMPLE 2
Preparation of a Compound of Formula II
Preparation of a Gadolinium-texaphyrin of Formula II
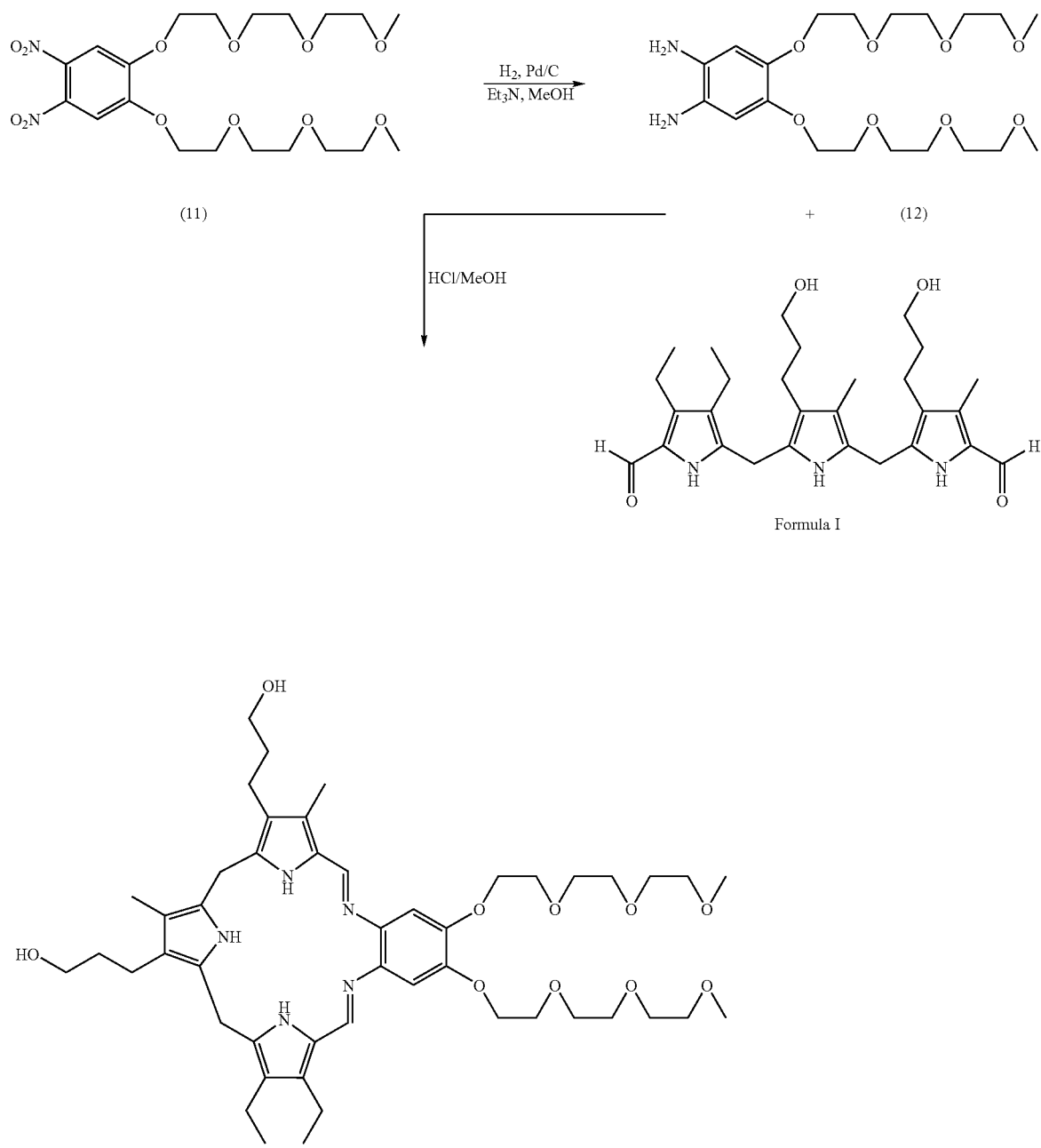

-continued

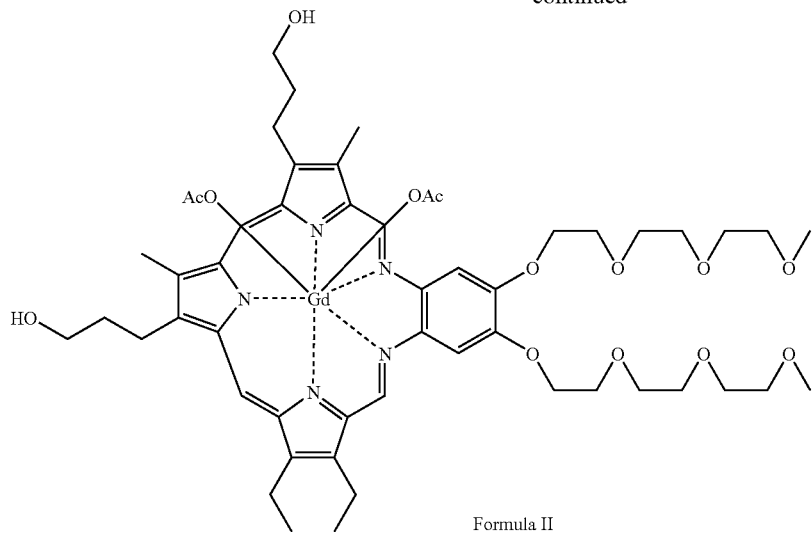

Formula II

A. Preparation of 23,24-Diethyl-16,17-bis(2-[2-(2-methoxyethoxy)ethoxy]ethoxy)-4,9-(3-hydroxypropyl)-5,10-dimethyl-13,20,25,26,27-pentaazapentacyclo[20.2.1.1$^{3,6}$.1$^{8,11}$.0$^{14,19}$]-heptacosa-3,5,8,10,12,14(19),15,17,20,22,24-undecaene 1,2-Bis(2-[2-(2-methoxyethoxy)ethoxy]ethoxy)-4,5-dinitrobenzene, a compound of formula (11) (1.21 g, 2.46 mmole), and 10% palladium on carbon (0.13 g) were added to a 250 mL Parr hydrogenation flask equipped with a rubber stopper. The reaction vessel was placed under a nitrogen atmosphere and methanol (20 mL) and triethylamine (0.4 mL, 3 mmol) were injected into the reaction vessel via syringe. The reaction vessel was placed under a pressurized hydrogen atmosphere (50 psi) on the Parr hydrogenator. The product, the diamino complex of formula (12) (≈2.46 mmol) in methanol was filtered directly into a 200 mL flask containing the non-symmetric tripyrrane of Formula I in which R$^1$ and R$^2$ are both ethyl, R$^3$ and R$^5$ are both 3-hydroxypropyl, R$^4$ and R$^6$ are both methyl, and R$_a$ and R$_b$ are both formyl (1.18 g, 2.27 mmol). Hydrochloric acid (0.42 mL, 4.98 mmol) was added to methanol (20 mL), and the acidified methanol was added to the reaction vessel. The reaction mixture was placed under a nitrogen atmosphere and wrapped in foil. The reaction was heated to 45° C. and allowed to stir for 90 minutes. The reaction was cooled, DARCO-activated charcoal (0.42 g) was added, and the mixture was allowed to stir for 1 hour. The suspension was filtered through a Celite pad directly into a tared, foil-covered flask. The solvent was removed under reduced pressure and the orange oil was dried overnight under high vacuum to yield the title compound.

B. Preparation of a Gadolinium (III) complex of 23,24-diethyl-16,17-bis(2-[2-(2-ethoxyethoxy)ethoxy]-ethoxy)-4,9-(3-hydroxypropyl)-5,10-dimethyl-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene, a Compound of Formula II The unmetallated macrocycle obtained in 2A above (2.00 g, 2.19 mmol, 82% purity), and gadolinium acetate (0.91 g, 2.73 mmole) were added to a 100 mL three-necked flask equipped with a stir bar, reflux condenser, inline gas bubbler, thermometer and gas dispersion tube. Methanol (50 mL) and triethylamine (3.1 mL, 22.2 mmol) were added to the flask. The reaction mixture was heated to reflux and allowed to stir for 40 minutes before air was passed through the dispersion tube at a minimal flow rate. The reaction was monitored by the ratio of UV-Vis absorbances at 354 nm and 474 nm. The reaction mixture was stirred at reflux for a total of approximately 7 hours, during which time the air flow was increased twice. The absorbance ration was 0.32 after 7 hours. The mixture was allowed to cool to room temperature and filtered through a Celite pad. The solvent was removed under reduced pressure, and the resulting solid was triturated in acetone (50 mL) for one hour. The suspension was filtered through a #1 filter paper and the filter cake was washed with acetone (10 mL), briefly air-dried and then dried overnight under a high vacuum. The solids (1.51 g, 1.31 mmol), obtained in 60% crude yield, were redissolved in methanol (40 mL) and water (4 mL). The solution was treated with acetic acid-washed zeolite (3×12 g) and then passed through a 2 cm diameter Bio-Rad column containing acetic acid-treated Ambersep resin (15 mL) at a rate of approximately 2 mL/min. The column was rinsed with methanol (30 mL). The green solution was concentrated under reduced pressure, and the residual water was azeotroped with 1-butanol (16 mL). The resulting solids were dried overnight at 35° C. under vacuum. The resulting solids (1.26 g, 1.10 mmol) were purified via preparative HPLC using a 28% acetonitrile/72% 100 mM ammonium acetate buffer isocratic region and a flow rate of 45 mL/min. Under these conditions, the main peak eluted at approximately 76 minutes (to 120 minutes). The other major peak was eluted in the gradient region (linear to 80:20 acetonitrile:buffer). The fractions were analyzed by HPLC and combined as appropriate. The acetonitrile was removed under reduced pressure, and the remaining solution was desalted by absorbing onto a tC18 Sep-Pack, rinsing with water and eluting with methanol. The solvent was removed under reduced pressure and the resulting solids were dried overnight. The solids were resuspended in acetone (15 mL), sonicated for 15 minutes, stirred for an additional 45 minutes and filtered through a #1 filter paper. The solids were rinsed with acetone until the rinse was pale yellow, and then briefly air-dried and dried overnight under vacuum, yielding a compound of Formula II in which M is gadolinium and Z is bis acetate, as a dark green solid (0.74 g, 0.64 mmole), in 29% overall yield and 97.7% purity. Elemental analysis calculated for $C_{52}H_{72}GdN_5O_{14} \cdot H_2O$: C, 53.34%; H, 6.39%; N, 6.00%; Gd, 13.48%. Obtained: C, 53.27%; H, 6.47%; N, 6.00%; Gd, 13.70%. Mass spectrometry. FABLR: 1030.7 (Calculated for M-2OAc: 1030.4). FABHR: 1030.4081 (Calculated for $C_{48}H_{66}{}^{158}Gd$: $N_5O_7$:1030.40507). ES: 1089.7 (Calculated for M-OAc: 1039.4). HPLC: 97.7% relative purity.

EXAMPLE 3

Preparation of a Compound of Formula II Preparation of a Texaphyrin of Formula II and a Dysprosium Metallotexaphyrin of Formula II

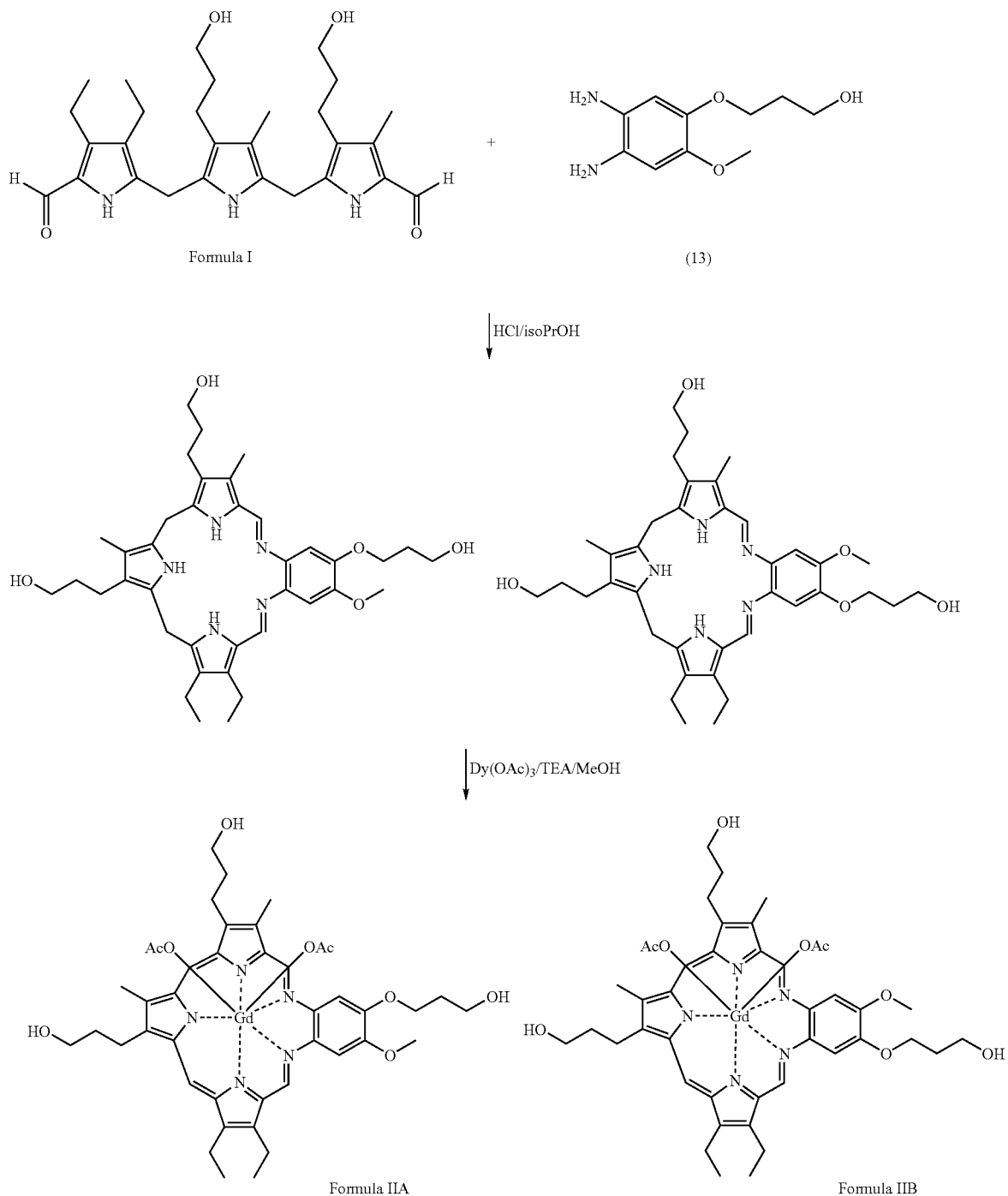

A. Preparation of a Mixture of 23,24-diethyl-16-(3-hydroxypropyloxy)-4,9-(3-hydroxypropyl)-17-methoxy-5,10-dimethyl-13,20,25,26,27-pentaazapentacyclo-[20.2.1.1$^{3,6}$.1$^{8,11}$.0$^{14,19}$]-heptacosa-3,5,8,10,12,14(19),15,17,20,22,24-undecaene of Formula II, and the 16-methoxy-17-(3-hydroxypropyloxy) Isomer In a 250 mL Parr flask, 1-(3-hydroxypropyl)oxy-2-methoxy-4,5-dinitrobenzene (0.3244 mmol), is dissolved in methanol (15 mL). Under a nitrogen atmosphere, 10% palladium on carbon (45 mg) is added, followed by concentrated hydrochloric acid (235 µL). The flask is placed on a Parr hydrogenation apparatus at a maintained hydrogen pressure of 40 psi. When consumption of hydrogen has ceased, the catalyst is removed by filtration over a pad of Celite® filter agent, and the resulting solution of 4,5-diamino-1-(3-hydroxypropyl)oxy-2-methoxybenzene, a compound of formula (13) in methanol, is transferred to a 100 mL single-neck flask containing the tripyrrane (compound of Formula I from Example 1; 0.3244 mmol) and a stir-bar. After dilution with methanol to a total volume of 45 mL, the reaction is heated to 55° C. After approx. 4 hours, the reaction is cooled in an ice bath and stirred for 10 minutes. The resulting precipitate is filtered and dried under high vacuum overnight. A second crop of crystals is collected and also dried under high vacuum. The solids are combined and dried for a further 2 hours to yield a mixture of the title compounds of Formula II in which R$^7$ is methoxy aand R$^8$ is 3-hydroxypropyloxy, or R$^8$ is methoxy and R$^7$ is 3-hydroxypropyloxy.

B. Preparation of a Mixture of Dysprosium (III) complex of 23,24-diethyl-16-(3-hydroxypropyl)oxy-4,9-(3-hydroxypropyl)-17-methoxy-5,10-dimethyl-13,20,25,26,27-pentaazapentacyclo-[20.2.1.1$^{3,6}$.1$^{8,11}$.0$^{14,19}$]heptacosa-1,3,5,7,9,11(27),12,14,16,18,20,22(25),23-tridecaene, a Metallated Compound of Formula II, and its 16-methoxy-17-(3-hydroxypropyloxy) Isomer In a 250 mL single-neck flask, fitted with a short condenser, the hydrochloride salt of the mixture of isomers obtained in Example 3A above (0.2326 mmol), dysprosium acetate hydrate (99 mg, 0.2907 mmol), triethylamine (195 µL, 1.395 mmol) and methanol (75 mL) are combined and heated at reflux open to the atmosphere. After 1.5 hours, methanol (75 mL) and triethylamine (65 µL, 0.465 mmol) are added to the reaction. After a total of about 6 hours, the reaction is cooled to room temperature, filtered over a pad of Celite® filter agent, and the solvents are removed by rotary evaporation under reduced pressure. After drying overnight under high vacuum, the residue is suspended in acetone (50 mL) and stirred for 1 hour at room temperature. The resulting solid is filtered, rinsed with acetone (10 mL), and dried under high vacuum overnight to afford the title compounds of Formula II in which R$^7$ is methoxy when R$^8$ is 3-hydroxypropyloxy, or R$^8$ is methoxy when R$^7$ is 3-hydroxypropyloxy, and M is dysprosium.

EXAMPLE 4

Preparation of 3,17,18,22-Tetraethyl-2,7,12,23-tetramethyl-8,13-bis(3-hydroxypropyl)sapphyrin, a Compound of Formula III

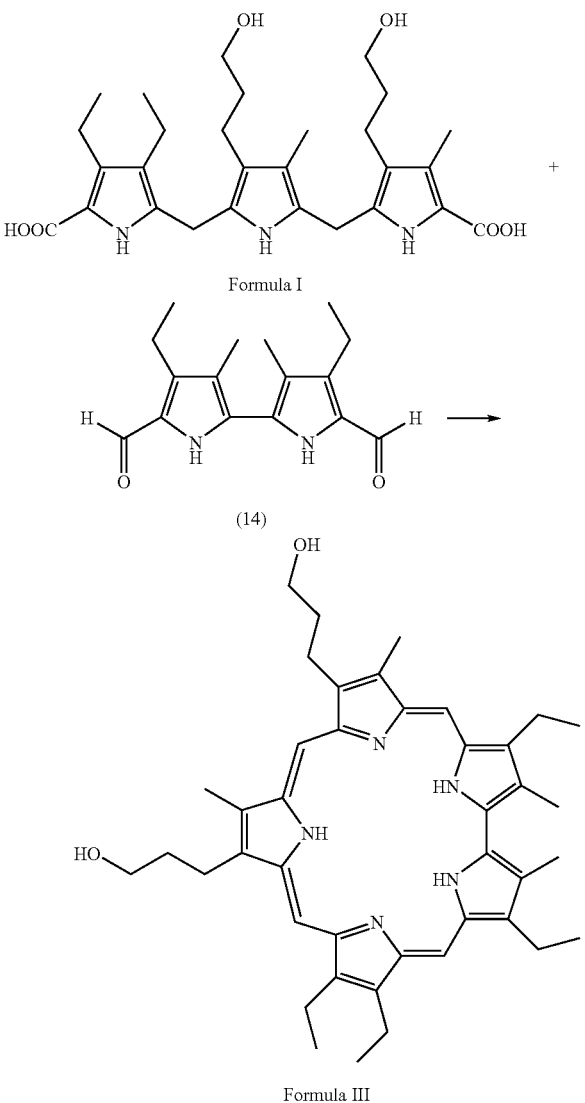

Starting Material

The 1,14-dicaboxytripyrrane of Formula I is prepared by oxidizing the corresponding bis-formyl tripyrranes, prepared as described in Example 1, with tin(IV) acetate, and working up the product by standard methods. This compound (0.06 mmol), and 4,4'-diethyl-5,5'-diformyl-3,3'-dimethyl-2,2'-bipyrrole, the compound of formula (14), are dissolved in 60 mL of absolute ethanol, and oxygen gas is bubbled through the solution. p-Toluenesulfonic acid monohydrate (0.24 mmol) is added, and oxygen bubbling is continued overnight. The solution is then evaporated on a rotary evaporator to dryness. The resulting solid is chromatographed on alumina (neutral) with 2.5% MeOH/CH$_2$Cl$_2$. The main fraction is collected, and the solvent is evaporated off to give the product of Formula III.

EXAMPLE 5

Preparation of Lutetium (III) Complex of 23,24-diethyl-16,17-bis(2-[2-(2-ethoxyethoxy)ethoxy]-ethoxy)-4,9-(3-hydroxypropyl)-5,10-dimethyl-3,20,25,26,27-pentaazapentacyclo[20.2.1.1$^{3,6}$.1$^{8,11}$.0$^{14,19}$]heptacosa1,3,5,7,9,11(27), 12,14,16,18, 20,22-(25), 23-tridecaene of Formula (16)

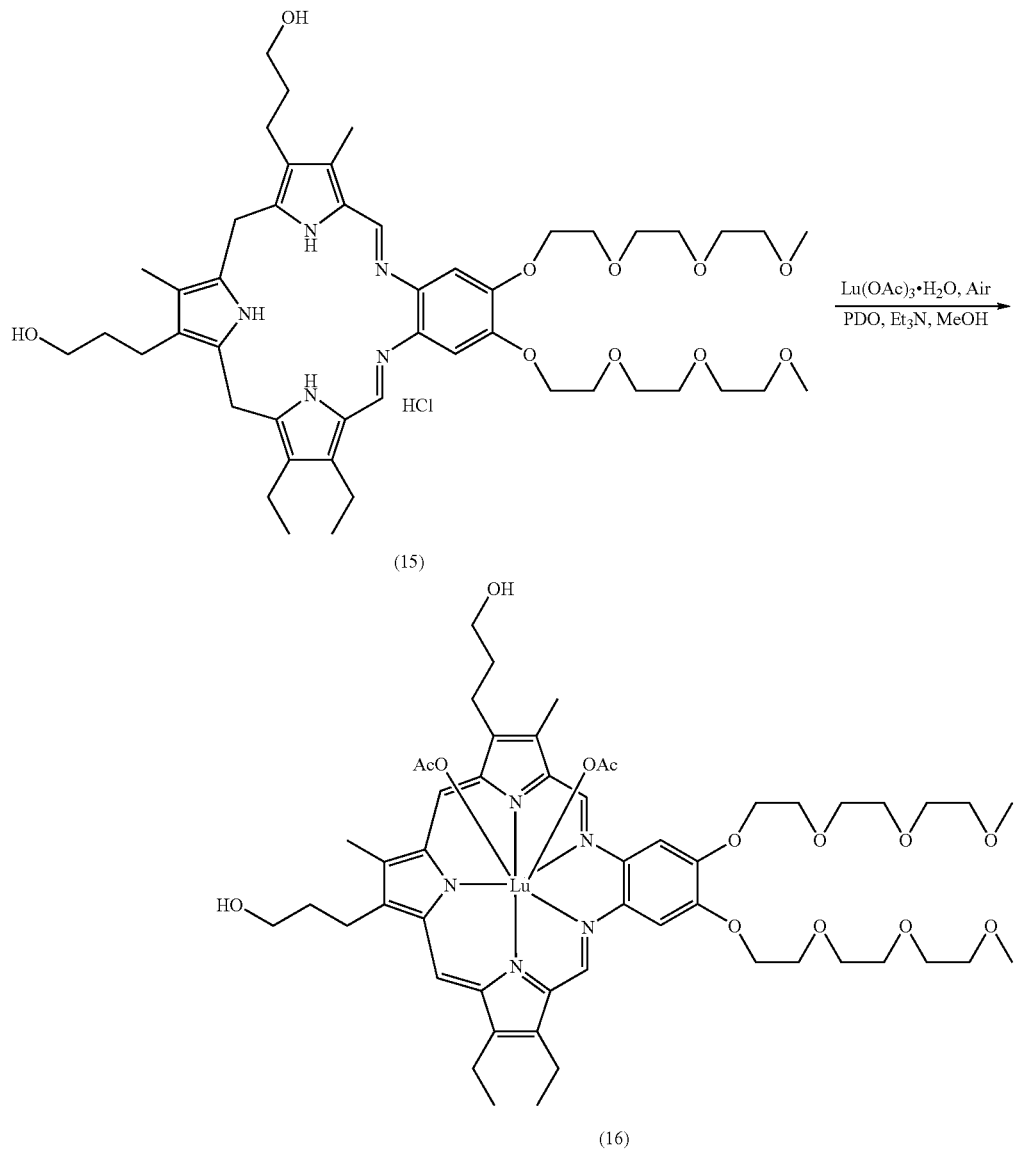

The nonaromatic macrocycle of formula (15) (2.40 g, 2.63 mmol) and lutetium acetate hydrate (1.39 g, 3.95 mmol) were added to a 250 mL three-necked flask equipped with a stir bar, reflux condenser, inline gas bubble, thermometer and gas dispersion tube. Methanol (120 mL), triethylamine (3.7 mL, 26.6 mmol) and 2,4-pentanedione (0.3 mL, 2.6 mmol) were added to the flask. The reaction mixture was heated to reflux and allowed to stir for one hour before 4% oxygen was passed through the dispersion tube at a minimal flow rate. The reaction was monitored by the ratio of UV-Vis absorbances at 354 nm and 474 nm. The reaction mixture was stirred at reflux for a total of approximately 6 hours, during which time the airflow was increased slowly. The absorbance ration was 0.28 after 6 hours. The mixture was allowed to cool to room temperature and filtered through a Celite pad. The solvent was removed under reduced pressure and the resulting solid was triturated in acetone (40 mL) for one hour. The suspension was filtered through a #1 filter paper and the filter cake washed with acetone (20 mL), briefly air dried and then dried overnight under a high vacuum. The solids (1.31 g, 1.13 mmol), obtained in 48% crude yield, were redissolved in methanol (100 mL) and water (10 mL). The solution was treated with acetic acid-washed zeolite (2×14 g) and then passed through a 2 cm diameter Bio-Rad column containing acetic acid-treated Ambersep resin (20 mL) at a rate of approximately 2 mL/min. The column was rinsed with methanol (40 mL). The green solution was concentrated under reduced pressure and dried overnight under vacuum. The resulting solids were redissolved in methanol (150 mL). Methyl isobutyl ketone (MIBK, 25 mL) was added drop-wise to the solution while stirring. The solution was concentrated to 100 mL under reduced pressure and additional MIBK (70 mL) was added drop-wise causing the product to precipitate out. The suspension was further concentrated under reduced pressure to a volume of 150 mL and a final aliquot of MIBK (55 mL) was added drop-wise. The suspension was again concentrated to a final volume of approximately 140 mL. The suspension was filtered through a #1 filter paper, rinsed with acetone (25 mL), briefly air-dried and dried overnight under vacuum. The title compound (16) was obtained in 44% yield, as a dark green solid (1.22 g, 1.05 mmol). Elemental analysis calculated for $C_{52}H_{72}LuN_5O_{14} \cdot H_2O$: C, 52.74%; H, 6.30%; N, 5.91%; Lu, 14.78%. Obtained: C, 52.42%; H, 6.38%; N, 5.97%; Lu, 14.94%. Mass spectrometry. FABLR: 1047.7 (Calculated for M-2OAc: 1047.4). FABHR: 1047.4209 (Calculated for $C_{48}H_{66}LuN_5O_{10}$: 1047.42174). ES: 1106.6 (Calculated for M-OAc: 1106.4).

EXAMPLE 6

Example 6 illustrates a synthesis of a compound of Formula I in which $R^1$ is diethla,imomethyl, $R^2$ is 3-hydroxypropyl, $R^3$ is a 2-(alaminoylamino)ethyl, $R^4$ is methyl, $R^5$ is acetyl, $R^6$ is acetic acid, and $R_a$ and $R_b$ are both formyl.

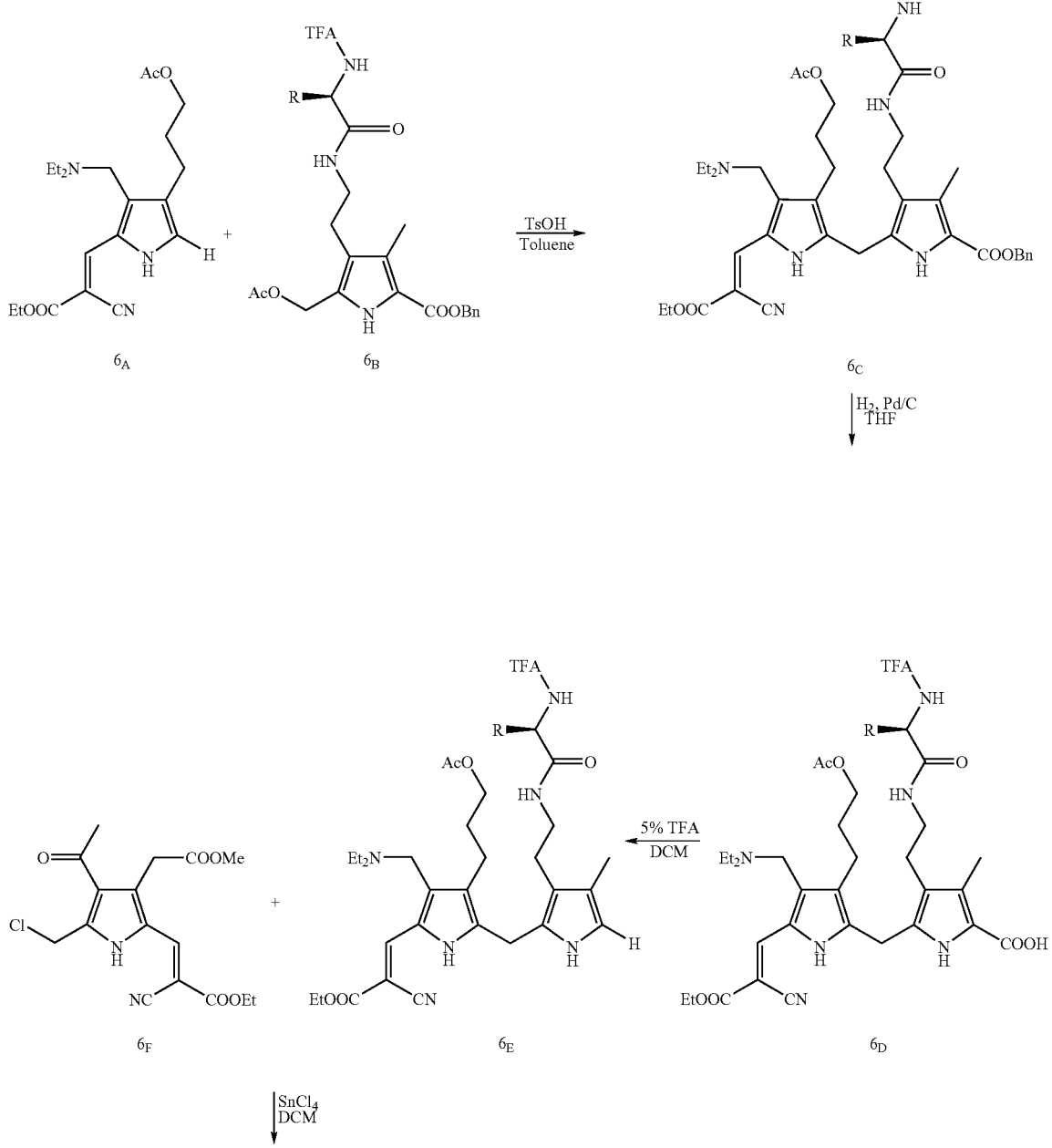

-continued
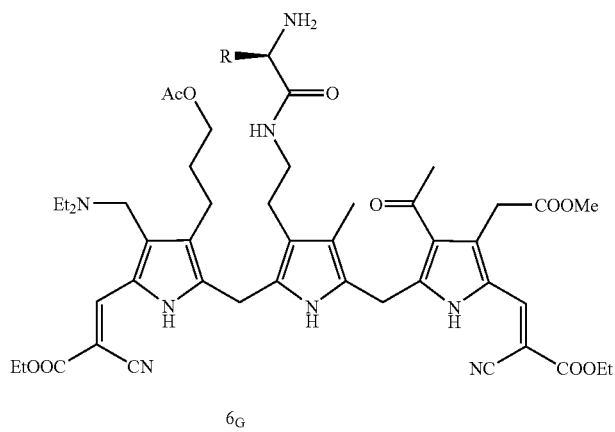
6<sub>G</sub>
KOH
EtOH, H₂O
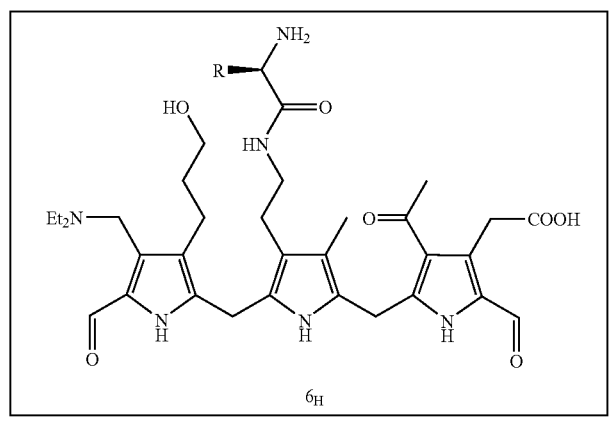
6<sub>H</sub>
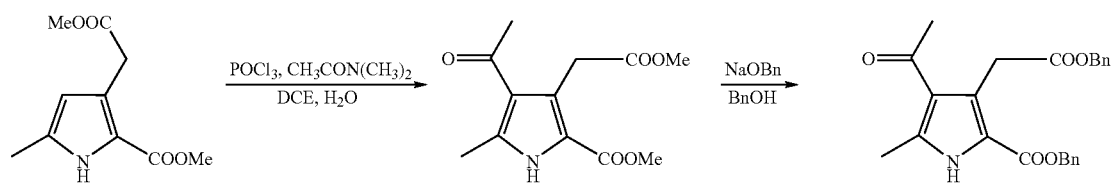
(*Dolphin*, Vol. 1 Part A, 110)
7<sub>O</sub>    7<sub>P</sub>    7<sub>Q</sub>
NaOMe
MeOH -continued

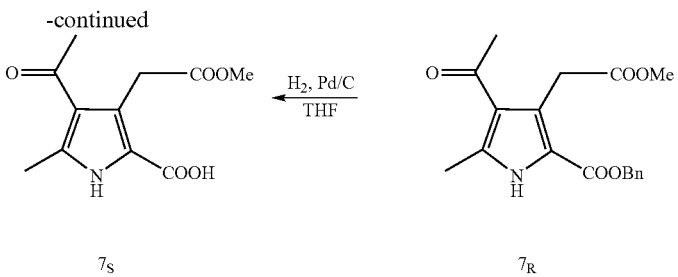

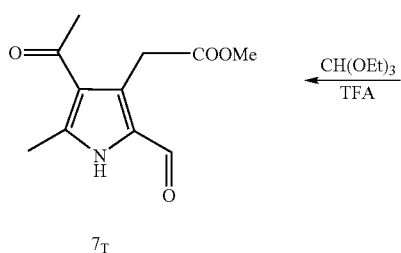

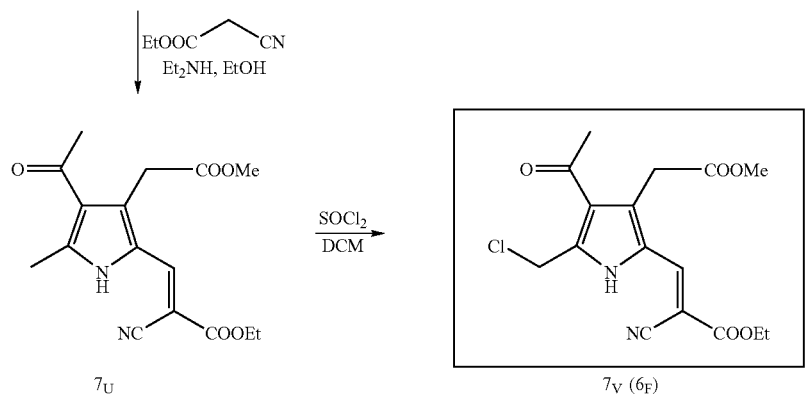

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:
1. A texaphyrin of Formula II:

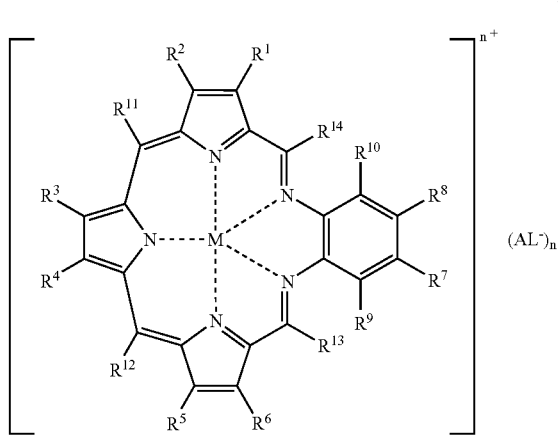

its hydrate, pharmaceutically acceptable salt, or a pro drug form thereof wherein, M is a monovalent, divalent, trivalent, or tetravalent metal cation;

$R^1$, $R^2$, $R^3$, $R^4$, $R^5$, $R^6$, $R^7$, and $R^8$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, optionally substituted haloalkyl, nitro, acyl, optionally substituted alkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl, and the group —X—Y, in which X is a covalent bond or a linker and Y is a catalytic group, a chemotherapeutic agent, or a with the proviso that $R^1$ is different from $R^6$, $R^2$ is different from $R^5$ and $R^5$ does not represent $(CH_2)_2$—CO—N $((CH_2)_2$—OH$)_2$, $CH_2CH_3$, or $(CH_2)_2$—CO—N$(CH_3)(CH_2$—$(CHOH)_4$—$CH_2$—OH$)$;

AL is an apical ligand; and n is an integer of 1–5.

2. The texaphyrin of claim 1, wherein $R^1$, $R^2$, $R^3$, $R^4$, $R^5$, $R^6$, $R^{11}$ and $R^{12}$ are independently chosen from the group consisting of hydrogen, optionally substituted alkyl, optionally substituted alkoxy, carboxyl, and optionally substituted carboxyalkyl, and $R^7$ and $R^8$ are independently chosen from the group consisting of hydrogen, hydroxy, optionally substituted alkyl, and optionally substituted alkoxy; and $R^9$ and $R^{10}$ are hydrogen.

3. The texaphyrin of claim 1, wherein $R^1$, $R^2$, $R^3$, $R^4$, $R^5$, $R^6$, $R^{11}$ and $R^{12}$ are independently chosen from the group consisting of hydrogen, optionally substituted alkyl, optionally substituted alkoxy, carboxyl, and optionally substituted carboxyalkyl, $R^7$ is chosen from the group consisting of hydrogen, hydroxy, optionally substituted alkyl, and optionally substituted alkoxy, $R^8$ is a site-directing molecule or a chemotherapeutic agent; and $R^9$ and $R^{10}$ are hydrogen.

4. The texaphyrin of claim 2, wherein $R^1$ and $R^2$ are ethyl; $R^4$ and $R^6$ are methyl; $R^3$ and $R^5$ are hydroxypropyl; $R^7$ and $R^8$ are independently hydrogen, hydroxy, methyl, methoxy, —OCH$_2$CH$_2$CH$_2$OH, or —O(CH$_2$CH$_2$O)$_3$CH$_3$; and $R^9$, $R^{10}$, $R^{11}$ and $R^{12}$ are all hydrogen.

5. A pharmaceutical composition comprising at least one pharmaceutically acceptable excipient and a therapeutically effective amount of a compound of claim 1.

* * * * *